(12) United States Patent
del Real Pena et al.

(10) Patent No.: US 11,738,134 B2
(45) Date of Patent: Aug. 29, 2023

(54) SYSTEMS FOR SUPPORTING MEDICAL FLUID BAGS AND RELATED METHODS

(71) Applicant: Fresenius Medical Care Holdings, Inc., Waltham, MA (US)

(72) Inventors: Diego Suarez del Real Pena, Mission, TX (US); Jose Eduardo Pena Martinez, Reynosa (MX); David Yuds, Hudson, NH (US); Jonathan Leclerc, Northborough, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 112 days.

(21) Appl. No.: 17/204,700

(22) Filed: Mar. 17, 2021

(65) Prior Publication Data
US 2022/0296790 A1  Sep. 22, 2022

(51) Int. Cl.
*A61M 1/00* (2006.01)
*A61M 1/28* (2006.01)

(52) U.S. Cl.
CPC .............. *A61M 1/69* (2021.05); *A61M 1/28* (2013.01); *A61M 2205/15* (2013.01);
(Continued)

(58) Field of Classification Search
CPC ...... A61M 1/69; A61M 1/28; A61M 2205/15; A61M 2205/3306; A61M 2205/3331; A61M 2205/3375; A61M 2205/3553; A61M 2205/502; A61M 1/284; A61M 2209/084
See application file for complete search history.

(56) References Cited

U.S. PATENT DOCUMENTS

| 4,393,880 A | 7/1983 | Taylor |
| 4,496,354 A | 1/1985 | Steer et al. |

(Continued)

FOREIGN PATENT DOCUMENTS

| CN | 304920989 S | 11/2018 |
| CN | 215448175 U | * 1/2022 |

(Continued)

OTHER PUBLICATIONS

BC Renal, "Warming Peritoneal Dialysis Solutions," BC Provincial Renal Agency, Jan. 2018, 14 pages.

(Continued)

*Primary Examiner* — Adam Marcetich
*Assistant Examiner* — Rachel O'Connell
(74) *Attorney, Agent, or Firm* — Fish & Richardson P.C.

(57) ABSTRACT

This disclosure relates to systems for supporting medical fluid bags and related methods. In some implementations, a system includes a curved tray configured to support a medical fluid bag during a medical treatment, the curved tray including a plurality of openings therethrough, a medical fluid collection basin removably coupled to the curved tray and configured to collect medical fluid leaked from the medical fluid bag during the medical treatment, a leak detector coupled to a surface of the medical fluid collection basin and configured to detect fluid as leaked from the medical fluid bag into the medical fluid collection basin, and a control unit configured to receive treatment data related to the medical treatment.

23 Claims, 18 Drawing Sheets

(52) U.S. Cl.
CPC .............. *A61M 2205/3306* (2013.01); *A61M 2205/3331* (2013.01); *A61M 2205/3375* (2013.01); *A61M 2205/3553* (2013.01); *A61M 2205/502* (2013.01)

(56) References Cited

U.S. PATENT DOCUMENTS

| | | | |
|---|---|---|---|
| 5,141,492 | A | 8/1992 | Dadson et al. |
| 5,445,610 | A | 8/1995 | Evert |
| 5,591,344 | A | 1/1997 | Kenley et al. |
| 5,782,796 | A | 7/1998 | Din et al. |
| 6,447,492 | B1 | 9/2002 | Frohn |
| 7,559,913 | B1 | 7/2009 | Jeppsson et al. |
| 8,692,140 | B1 * | 4/2014 | Pollock .................. A61B 50/37 177/15 |
| 9,147,045 | B2 | 9/2015 | Yu et al. |
| D800,909 | S | 10/2017 | Jones |
| D850,959 | S | 6/2019 | Zeyher et al. |
| D851,257 | S | 6/2019 | Zeyher et al. |
| D869,971 | S | 12/2019 | Zeyher et al. |
| 2002/0082569 | A1 | 6/2002 | Wildman |
| 2004/0215129 | A1 | 10/2004 | Edgson et al. |
| 2005/0133674 | A1 | 6/2005 | Sobue et al. |
| 2007/0178197 | A1 * | 8/2007 | LaRue ................. B65D 81/262 206/204 |
| 2009/0187138 | A1 * | 7/2009 | Lundtveit ........... A61M 1/1619 604/29 |
| 2010/0010425 | A1 | 1/2010 | Yu et al. |
| 2014/0074018 | A1 * | 3/2014 | Childers .............. A61M 1/282 604/28 |
| 2014/0199057 | A1 * | 7/2014 | Hansen ............... A61M 1/1664 392/443 |
| 2018/0236157 | A1 | 8/2018 | Wolf et al. |
| 2018/0289879 | A1 * | 10/2018 | Fulkerson ............. A61M 1/267 |
| 2019/0275217 | A1 * | 9/2019 | Suarez del Real Pena ................. A61M 39/10 |
| 2019/0307939 | A1 | 10/2019 | Lo et al. |
| 2019/0381229 | A1 | 12/2019 | Biewer et al. |
| 2021/0023289 | A1 * | 1/2021 | Hansen ................. A61M 1/287 |
| 2021/0069399 | A1 * | 3/2021 | Egley .................... A61M 1/367 |

FOREIGN PATENT DOCUMENTS

| | | |
|---|---|---|
| DE | 19655224 | 11/2006 |
| JP | 2014-083369 A | 5/2014 |

OTHER PUBLICATIONS ispd.org [online], "Questions About PD," Feb. 8, 2013, retrieved from URL <https://ispd.org/question/any-other-recommendations-for-warming-of-pd-fluids-in-home-capd-in-places-where-warming-plates-are-costly-could-electric-blankets-be-recommended-while-such-use-has-not-been-mentioned-by-the-manufactu/>, retrieved on Jun. 7, 2021, 2 pages.

Mohamed, "Differential Diagnosis of Cloudy effluent in Peritoneal Dialysis," Presented at DaVita Buraydah Center 2016, Feb. 13, 2016, retrieved from URL <https://www.slideshare.net/ssuser79d8c1/differential-diagnosis-of-cloudy-effluent-in-peritoneal-dialysis>, retrieved on Jun. 7, 2021, 34 pages.

PCT International Search Report and Written Opinion in International Application No. PCT/US2022/018269, dated Jul. 6, 2022, 19 pages.

\* cited by examiner

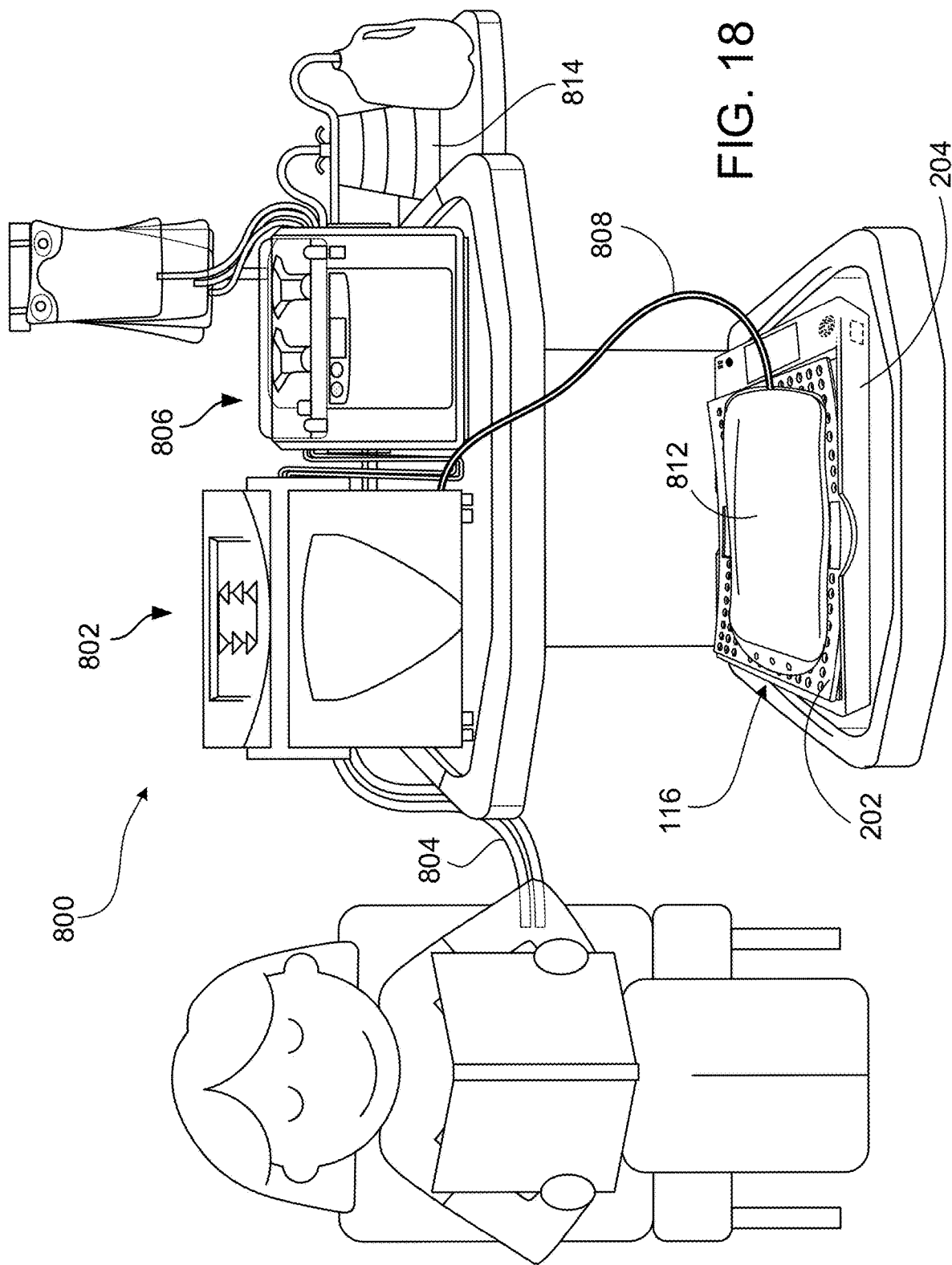

SYSTEMS FOR SUPPORTING MEDICAL FLUID BAGS AND RELATED METHODS

TECHNICAL FIELD

This disclosure relates to systems for supporting medical fluid bags and related methods.

BACKGROUND

Dialysis is a treatment used to support a patient with insufficient renal function. The two principal dialysis methods are hemodialysis and peritoneal dialysis. During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), the patient's peritoneal cavity is periodically infused with dialysate. The membranous lining of the patient's peritoneum acts as a natural semi-permeable membrane that allows diffusion and osmosis exchanges to take place between the solution and the blood stream. These exchanges across the patient's peritoneum result in the removal of waste products, including solutes like urea and creatinine, from the blood, and regulate the levels of other substances, such as sodium and water, in the blood.

Continuous ambulatory peritoneal dialysis (CAPD) therapy involves hanging a bag of fresh dialysate and using gravity to fill a patient's peritoneal cavity. At the end of the dwell phase of the treatment cycle, the patient drains effluent (spent dialysate) from the patient's peritoneal cavity into a drain bag via gravity.

SUMMARY

In one aspect, a system includes a curved tray configured to support a medical fluid bag during a medical treatment, the curved tray comprising a plurality of openings therethrough, a medical fluid collection basin removably coupled to the curved tray and configured to collect medical fluid leaked from the medical fluid bag during the medical treatment, a leak detector coupled to a surface of the medical fluid collection basin and configured to detect fluid as leaked from the medical fluid bag into the medical fluid collection basin, and a control unit configured to receive treatment data related to the medical treatment.

Implementations can include one or more of the following features in any combination.

In some implementations, the control unit is configured to receive a signal from the leak detector indicating that a medical fluid leak occurred during the medical treatment.

In certain implementations, the control unit is configured to transmit the treatment data to one or more computing devices.

In some implementations, the treatment data includes at least one of a drain start time, a drain end time, a drain duration, a volume drained, and leakages detected.

In certain implementations, the control unit is configured to automatically transmit treatment data to a remote computing device.

In some implementations, the medical fluid collection basin includes a port, and the control unit is configured to transmit the treatment data to a portable memory device interfacing with the port of the medical fluid collection basin.

In certain implementations, the portable memory device is a universal serial bus (USB) memory device, and the port is a USB port.

In some implementations, the port is configured to connect to a flow sensor.

In certain implementations, the flow sensor is configured to measure fluid flow along a fluid line fluidly coupled to a dialysate bag and a peritoneal cavity of a patient, and the control unit is configured to determine a fill volume based on the fluid flow measured by the flow sensor.

In some implementations, the medical fluid collection basin includes a drain opening therethrough.

In certain implementations, the medical fluid collection basin includes a drain plug configured to be inserted into and seal the drain opening during the medical treatment.

In some implementations, the medical fluid collection basin includes a curved inner surface that slopes towards the drain.

In certain implementations, the curved inner surface of the medical fluid collection basin includes a clear material.

In some implementations, the leak detector is positioned proximate the center of the medical collection basin.

In certain implementations, the leak detector includes a pair of metal rings surrounding a weight scale coupled to the medical fluid collection basin.

In some implementations, the curved tray includes a central channel configured to direct liquid leaked from the medical fluid bag into the medical fluid collection basin.

In certain implementations, the curved tray includes handles.

In some implementations, the curved tray includes text on a surface of the curved tray configured to be in contact with the medical fluid bag.

In certain implementations, the system includes a weight scale coupled to the medical fluid collection basin and configured to contact the curved tray, wherein the weight scale is configured to detect a weight of fluid contained within a medical fluid bag positioned on the curved tray.

In some implementations, the control unit is configured to receive data from the weight scale and to determine, based on the data, an amount of fluid contained within the medical fluid bag positioned on the curved tray.

In certain implementations, the control unit is configured to determine, based on data received from the weight scale, treatment data comprising at least one of a drain start time, a drain end time, or a drain duration.

In some implementations, the medical fluid collection basin comprises a speaker.

In certain implementations, the medical fluid collection basin comprises a microphone communicably coupled to the control unit and configured to receive user input regarding one or more treatment parameters.

In some implementations, the medical fluid collection basin comprises a graphical display configured to display a graphical user interface.

In certain implementations, the system includes one or more wheels coupled to a bottom surface of the medical fluid collection basin.

In some implementations, the medical fluid bag is a drain bag configured to receive effluent draining out of a patient during the medical treatment.

In certain implementations, the system includes an effluent sensor coupled to the medical fluid collection basin and configured to detect one or more characteristics of effluent draining out of a patient into the medical fluid bag during the medical treatment.

In some implementations, the effluent sensor is an optical sensor or an ultrasonic sensor.

In certain implementations, the system includes a heater configured to heat a medical fluid contained in the medical fluid bag positioned on the curved tray.

In some implementations, the medical fluid bag includes a dialysate bag containing dialysate to be provided to a patient during the medical treatment; and the heater is configured to heat the dialysate to a predetermined temperature.

In certain implementations, the heater includes a conducting core element extending through the curved tray, and a heating element coupled to a surface of the medical fluid collection basin, wherein contact between the conducting core element and the heating element heats the conducting core element.

In some implementations, the system includes one or more depressible members coupled to the medical fluid collection basin and configured to contact the curved tray, wherein placing a filled fluid bag on the curved tray compresses the one or more depressible members and causes the conducting core element to contact the heating element.

In certain implementations, the heating element is an induction heating element.

In some implementations, the medical treatment is a peritoneal dialysis treatment.

In certain implementations, the medical treatment is a hemodialysis treatment, a hemofiltration treatment, or a hemodiafiltration treatment.

In some implementations, the medical fluid bag contains dialysate or effluent drained from a patient during the medical treatment.

In a further aspect, a system includes a blood treatment machine and a basin system. The basin system includes a curved tray configured to support a medical fluid bag during a medical treatment performed using the blood treatment machine, the curved tray comprising a plurality of openings therethrough, a medical fluid collection basin removably coupled to the curved tray and configured to collect medical fluid leaked from the medical fluid bag during the medical treatment, a leak detector coupled to a surface of the medical fluid collection basin and configured to detect fluid as leaked from the medical fluid bag into the medical fluid collection basin, and a control unit configured to receive treatment data related to the medical treatment.

In a further aspect, a method of recording treatment data related to a medical treatment includes positioning a medical fluid bag on a tray coupled to a basin device, flowing fluid into the medical fluid bag during the medical treatment, detecting leakage of fluid from the medical fluid bag using a leak detection sensor positioned on a surface of the basin device, and automatically transmitting treatment data from a control unit of the basin device to a remote computing device, the treatment data indicating that a medical fluid bag leak has occurred during the medical treatment.

In a further aspect, a system includes a tray configured to support a medical fluid bag during a medical treatment, a medical fluid collection basin coupled to the tray, a conducting core element extending through the tray, and a heating element coupled to a surface of the medical fluid collection basin, wherein contact between the conducting core element and the heating element heats the conducting core element.

Implementations can include one or more of the following features in any combination.

In some implementations, the system includes one or more depressible members coupled to the medical fluid collection basin and configured to contact the tray, wherein placing a filled fluid bag on the tray compresses the one or more depressible members and causes the conducting core element to contact the heating element.

In certain implementations, the heating element is an induction heating element.

In some implementations, the system includes an effluent sensor coupled to the medical fluid collection basin and configured to detect one or more characteristics of effluent draining out of a patient into the medical fluid bag during the medical treatment.

In certain implementations, the effluent sensor is an optical sensor or an ultrasonic sensor.

In some implementations, the medical fluid bag contains dialysate fluid to be provided to a patient during the medical treatment.

Implementations can include one or more of the following advantages.

In some implementations, a basin system enables rapid detection of a leakage from a medical fluid bag (e.g., a dialysate bag or a drain bag) being used during a medical treatment (e.g., a dialysis treatment). The basin system can also alert a user of the system if a leakage from the medical fluid bag is occurring. By automatically detecting leaks from fluid bags used during the treatment and alerting a user, corrective action to stop the leak can be quickly provided to prevent additional fluid leakage.

In some implementations, the basin system automatically detects and records the weight of fluid in a medical fluid bag being used during a medical treatment. By automatically detecting and recording the amount of fluid contained in the medical fluid bag, patient errors and measurement inaccuracies during data collection can be avoided.

In some implementations, the basin system can provide improved analysis of the clarity of a medical fluid. For example, in some implementations, a tray used to support a drain bag during a drain phase of a PD treatment includes one or more markings that can be used to visually determine the clarity of effluent contained in the drain bag. In some implementations, the basin system includes an effluent sensor to automatically detect effluent clarity. These improved systems for checking effluent clarity during a drain phase can lead to improved patient safety.

In some implementations, the basin system permits automated recording and transmission of treatment data. For example, a control unit of the basin system can automatically collect treatment data using one or more components of the basin system, and the control unit can automatically transmit the collected treatment data to one or more remote computing devices for storage and/or processing of the treatment data. By automatically collecting treatment data and transmitting treatment data to remote computing devices, patient errors and measurement inaccuracies during data collection can be avoided, and the overall treatment time can be reduced.

In some implementations, the basin system is designed to be portable. For example, the basin system can include one or more wheels, making the system easy to move between treatments.

In addition, the basin system can provide safe and effective heating of medical fluid contained in medical fluid bags. For example, the basin system can include a heating system that is configured to heat medical fluid contained in a medical fluid bag placed on a tray of the basin system. The heating system is configured to stop heating upon removal of the fluid bag from the tray. By automatically stopping the heating in response to the fluid bag being removed from the tray, efficiency of the heating system and patient safety is improved.

The details of certain implementations are set forth in the accompanying drawings and the description below. Other aspects, features, and advantages will be apparent from the description and drawings, and from the claims.

DESCRIPTION OF DRAWINGS

FIG. 18 is an illustration of a blood treatment system including a basin system supporting a fluid bag.

Like reference symbols in the various drawings indicate like elements.

DETAILED DESCRIPTION

Figure 1:
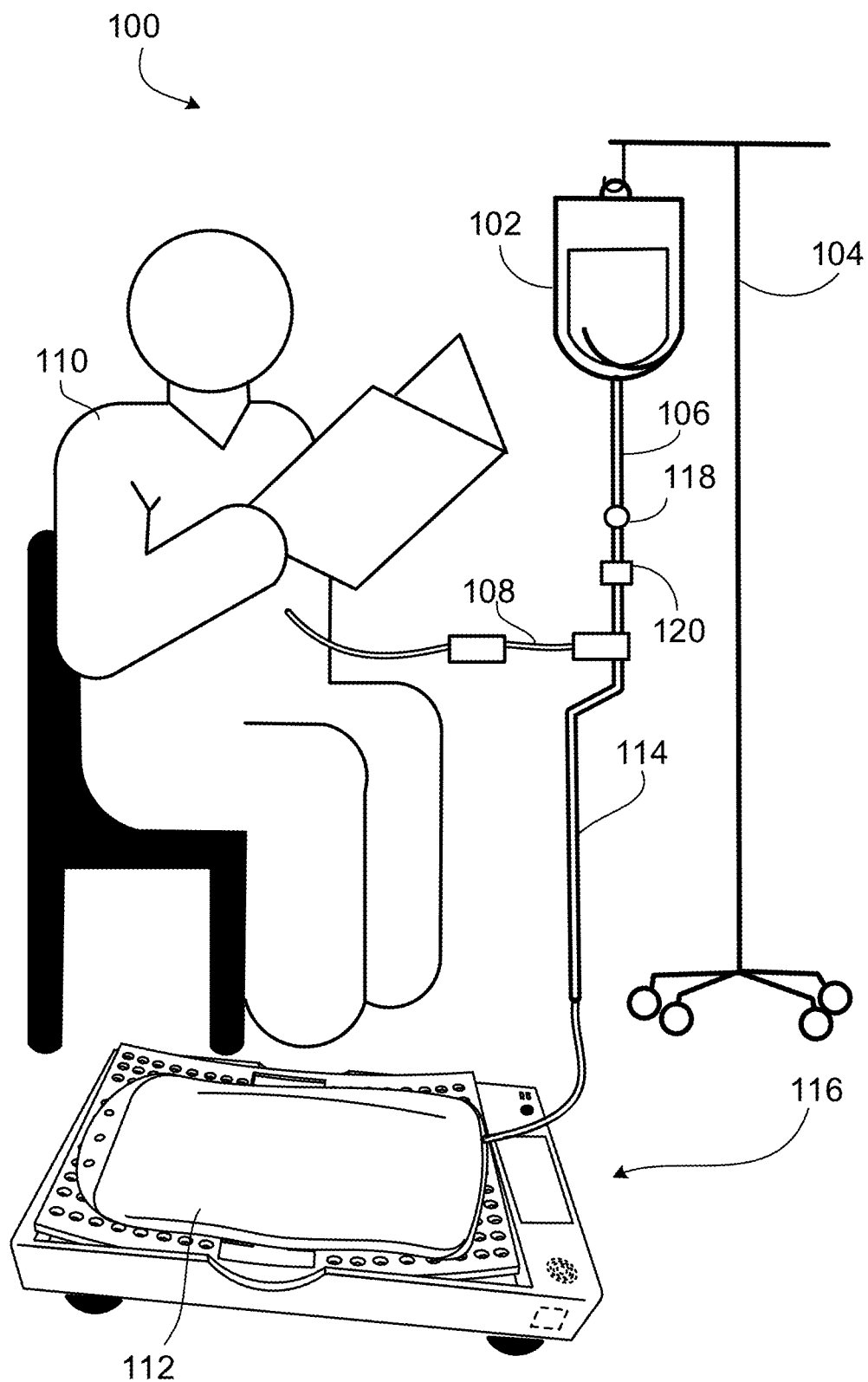
FIG. 1 is an illustration of a patient receiving peritoneal dialysis (PD) treatment using an example PD treatment system.

FIG. 1 depicts a patient 110 receiving a peritoneal dialysis ("PD") treatment using a PD system 100. The PD system 100 includes a dialysate bag 102 suspended from a stand 104. A fluid line 106 connects the dialysate bag 102 to a transfer set 108 that is connected to the patient 110. A drain bag 112 is fluidly connected to the transfer set 108 via fluid line 114. The PD system 100 includes a basin system 116 on which the drain bag 112 is positioned during treatment.

The PD system 100 of FIG. 1 can be used to perform a continuous ambulatory peritoneal dialysis (CAPD) treatment. CAPD treatment typically begins by draining fluid from a patient's peritoneal cavity. Once the patient's peritoneal has been drained, the patient's peritoneal cavity is filled with a fluid (e.g., dialysate), which then dwells in the patient's peritoneal cavity. After delivering the dialysate to the patient's peritoneal cavity and permitting the dialysate to dwell in the peritoneal cavity for a predetermined period of time, the dialysate is drained from the peritoneal cavity. These processes of draining, filling, dwelling, and draining is repeated throughout a CAPD treatment cycle.

In order to drain fluid from the patient's peritoneal cavity, the PD system 100 includes a drain bag 112 that is fluidly connected to the patient's peritoneal catheter using the transfer set 108. During the drain phase of the PD treatment, the drain bag 112 is coupled to the patient's transfer set 108 using a fluid line 114, and fluid flows from the peritoneal cavity of the patient 110 into the drain bag 112 along fluid line 114. The drain bag 112 is positioned on and supported by the basin system 116 during the drain phase of the PD treatment.

Once the patient's peritoneal cavity has been drained of fluid, the fill phase of the PD treatment can be performed by connecting the dialysate bag 102 filled with dialysate to the patient's peritoneal catheter using the transfer set 108, and delivering about 1-3 liters of dialysate to the peritoneal cavity. As will be described in further detail herein, in some implementations, the dialysate in the dialysate bag 102 is heated prior to beginning the fill phase.

In order to fill the patient's peritoneal cavity with dialysate without the use of a pump, the dialysate bag 102 is positioned above the transfer set 108, which allows for gravity filling of the patient's peritoneal cavity. By hanging the dialysate bag 102 on the stand 104, the dialysate flows downwards via gravity along the fluid line 106 and into the transfer set 108. A clamp 118 is provided along the fluid line 106 to control fluid flow from the dialysate bag 102 along the fluid line 106. For example, once the dialysate bag 102 has been attached to the stand 104 and opposite ends of the fluid line 106 are coupled to the dialysate bag 102 and the transfer set 108, which is coupled to the patient's peritoneal catheter, the clamp 118 along the fluid line 106 can be opened to allow dialysate to flow via gravity from the dialysate bag 102 along the fluid line 106, through the transfer set 108 and the patient's catheter, and into the peritoneal cavity of the patient 110.

As will be described in further detail herein, the basin system 116 can assist a user in performing the PD treatment. For example, during PD treatment, the patient 110 or another user typically monitors and records various data related to the treatment, such as the dialysate concentration, the dialysate expiry date, dialysate volume exchanged during treatment, fill start time, fill end time, dwell time, drain start time, drain end time, the amount of fluid drained during the treatment, the clarity of effluent drained during the treatment. As will be described in detail herein, the basin system 116 can be used to assist the patient 110 in monitoring and recording such data related to the PD treatment. The basin system 116 can also be used to heat dialysate fluid contained in the dialysate bag 102 prior to flowing the dialysate in the dialysate bag 102 to the peritoneum of the patient 110, as will be described below.

Figure 2:
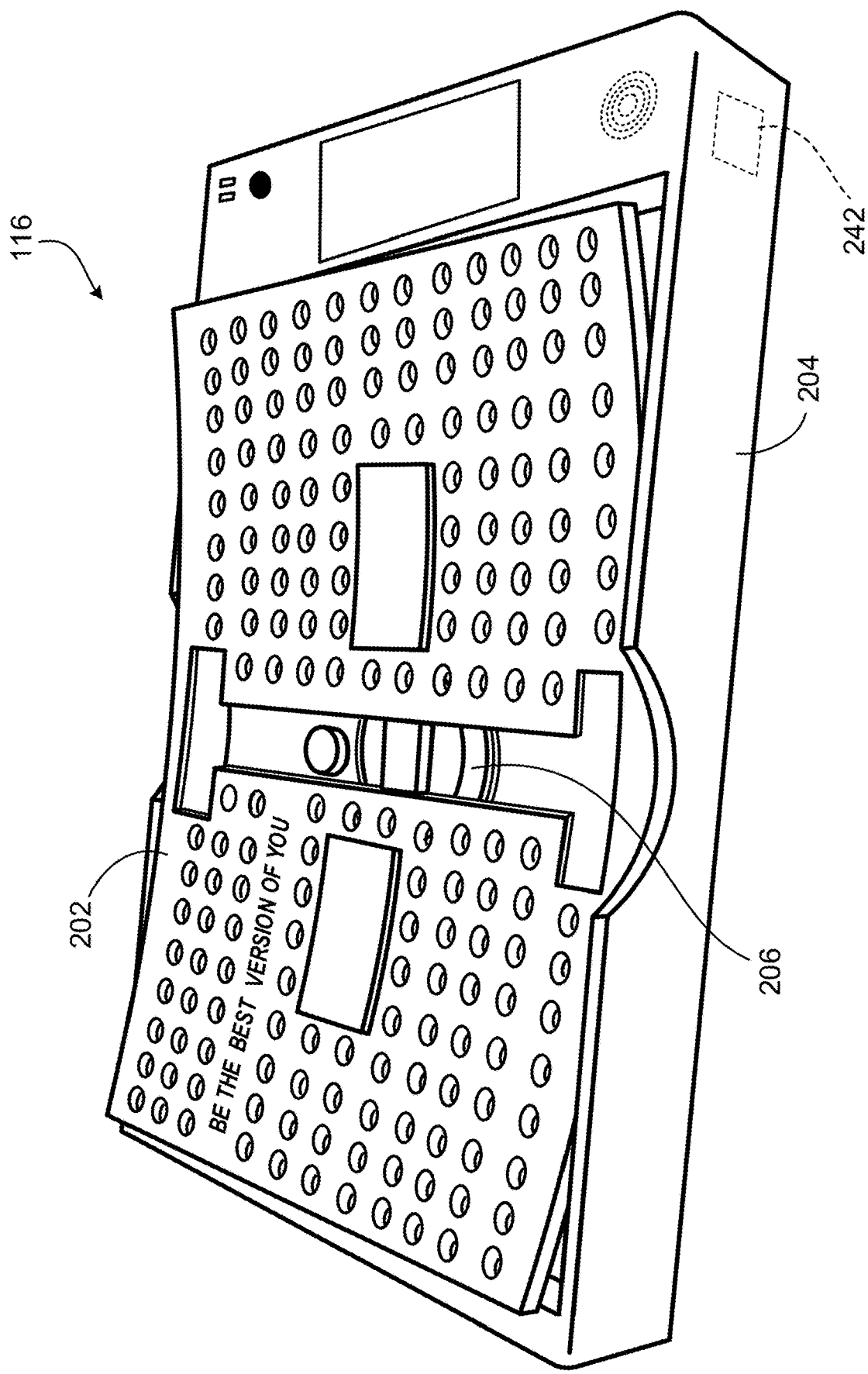
FIG. 2 is a perspective view of a basin system for supporting fluid bags of the PD system of FIG. 1.
Figure 3:
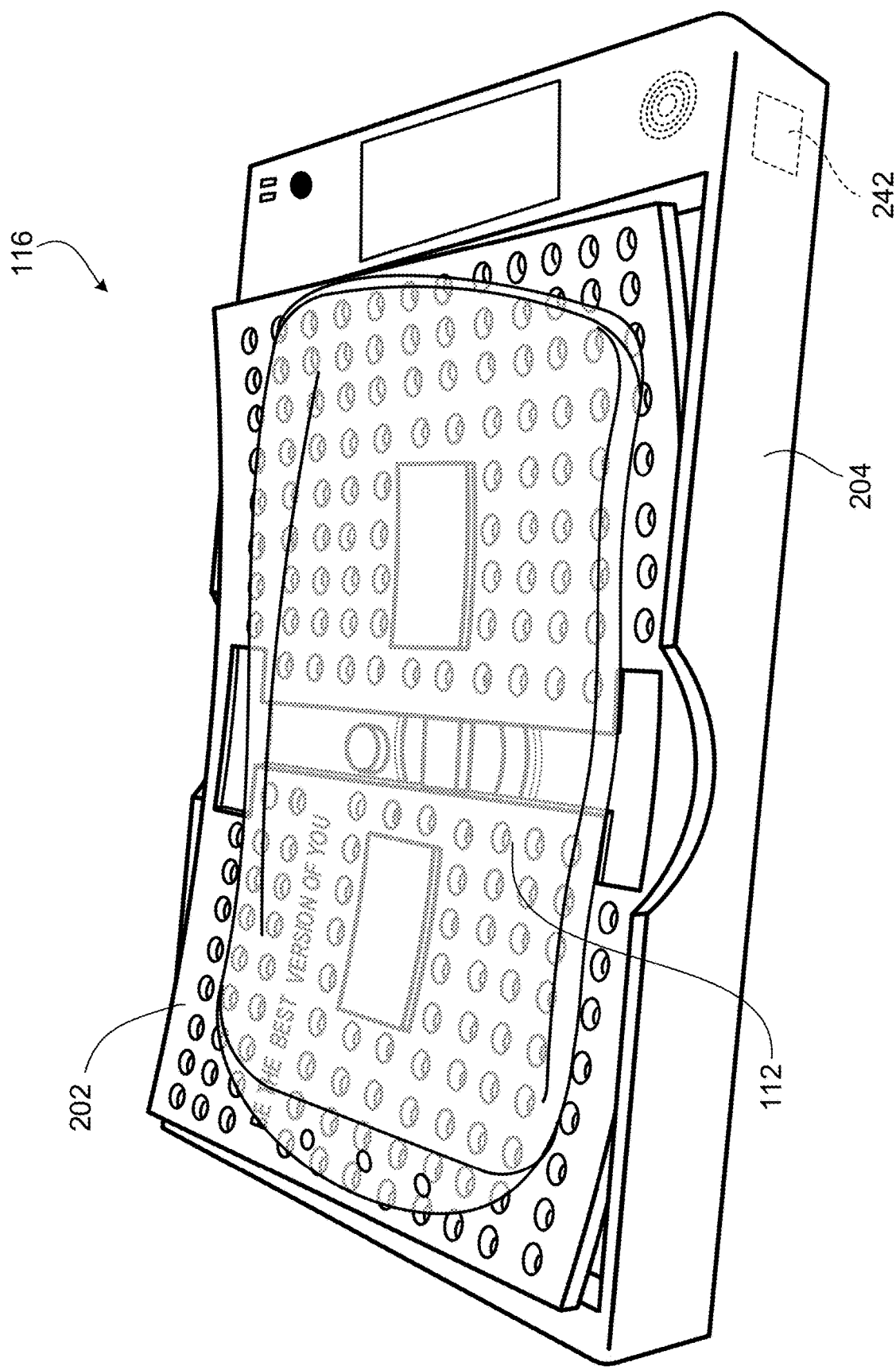
FIG. 3 is a perspective view of the basin system of FIG. 2 supporting a fluid bag of the PD system of FIG. 1.

FIG. 2 depicts an example basin system 116 for use during PD treatment. As can be seen in FIG. 2, the basin system 116 includes a tray 202 and a basin 204. The tray 202 is positioned on top of the basin 204 in order to support and position a fluid bag, such as the dialysate bag 102 or the drain bag 112, over the basin 204 during a PD treatment. For example, during the drain phase of the PD treatment, the drain bag 112 is positioned on the tray 202 over the basin 204, as depicted in FIG. 3. During a dialysate heating step prior to the fill phase of the PD treatment, the dialysate bag 102 is positioned on the tray 202 over the basin 204.

Figure 4:
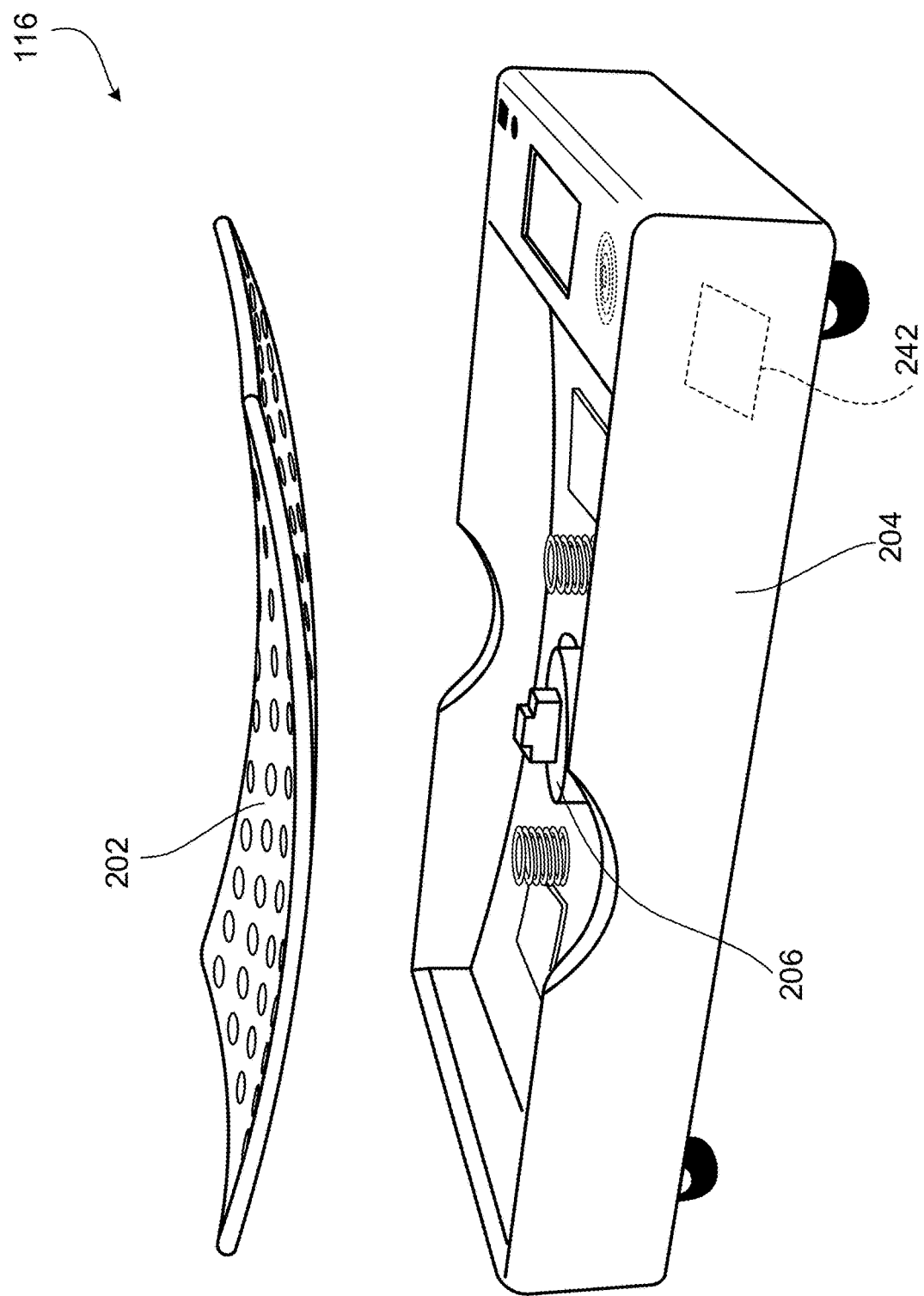
FIG. 4 is an exploded view of the basin system of FIG. 2.

As depicted in FIGS. 2 and 4, the basin 204 includes a weight scale 206, and the tray 202 is positioned over and in contact with the weight scale 206 during PD treatment. As will be described in further detail herein, the weight scale 206 can be used to measure the weight or changes in weight to the dialysate bag 102 and/or the drain bag 112 positioned on the tray 202 in order to determine various data for the treatment cycle. The data can include, for example, a drain start time, a drain end time, the length of time elapsed during the drain phase, and an amount of fluid drained from the patient, and a volume of fluid contained in a dialysate bag that is warmed prior to the fill phase of treatment using the basin system 116.

Figure 5:
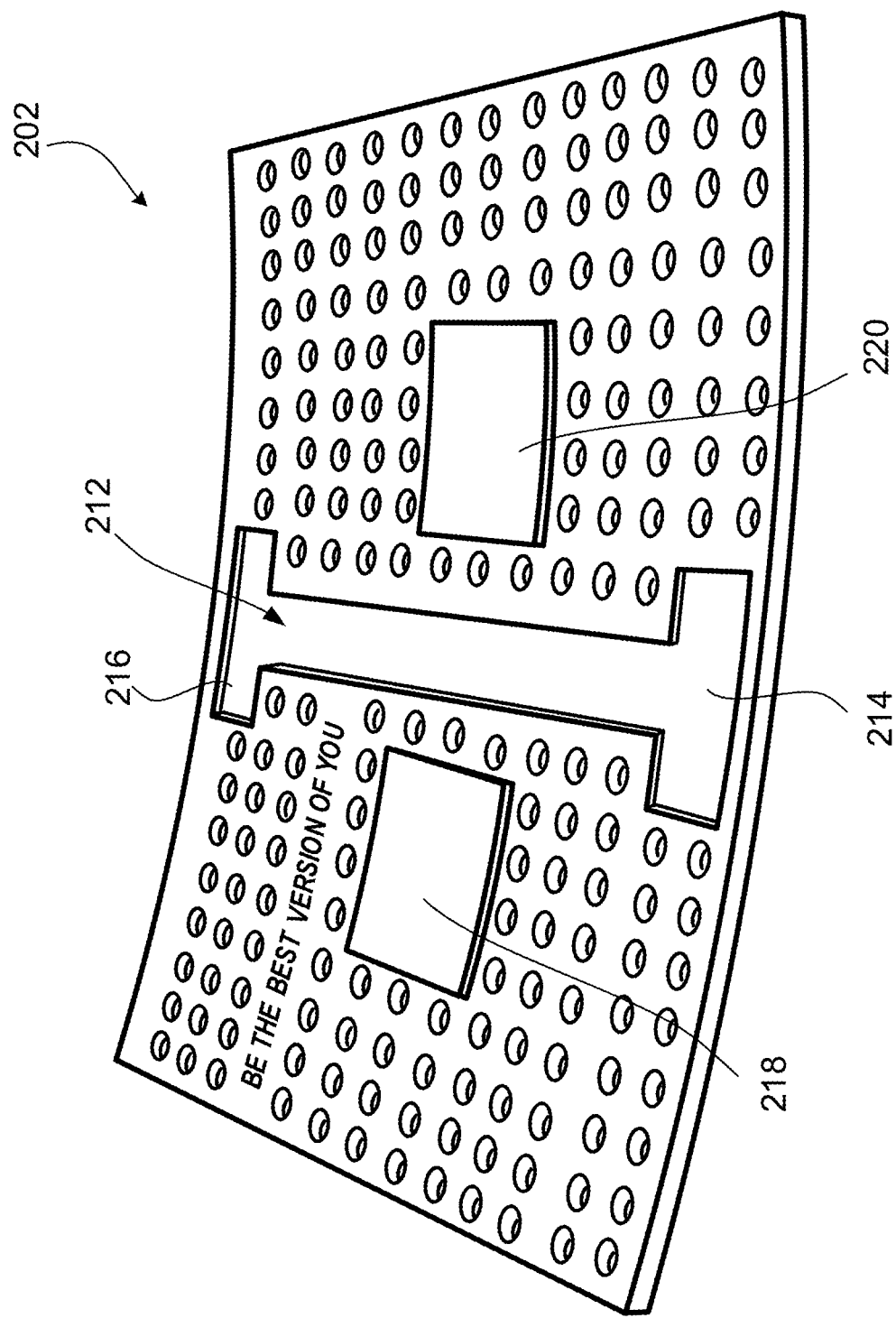
FIG. 5 is a perspective view of a tray of the basin system of FIG. 2.
Figure 6:
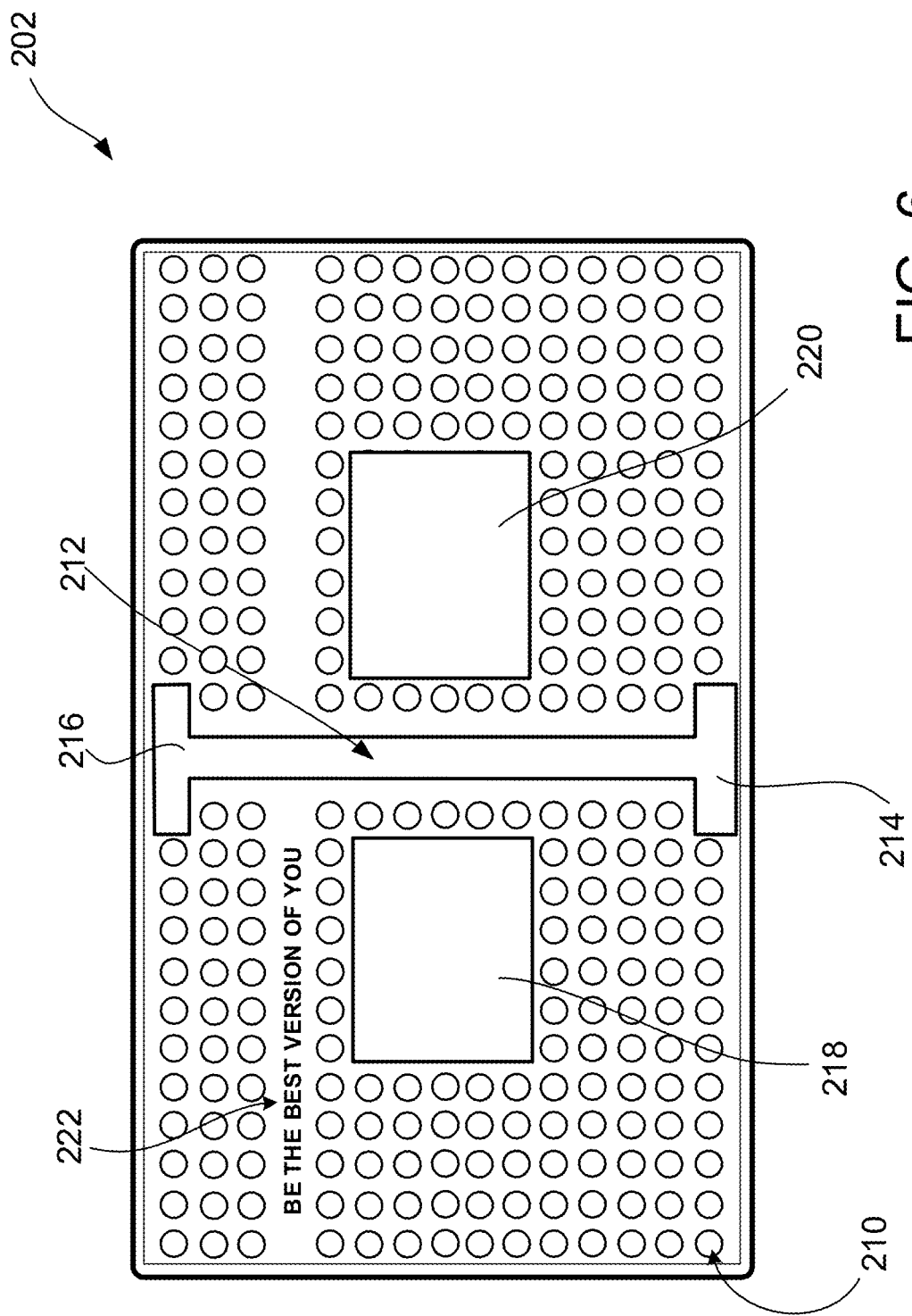
FIG. 6 is a top view of the tray of FIG. 5.

FIGS. 5 and 6 show the tray 202 that can be used to support the dialysate bag 102 and/or the drain bag 112 over the basin 204 during treatment. As can be seen in FIGS. 5 and 6, the tray 202 defines a number of openings 210 therethrough that allow fluid to flow through the tray 202 into the basin 204 when the tray 202 is positioned over the basin 204. For example, if the drain bag 112 or the dialysate bag 102 positioned on the tray 202 has a leak, fluid leaked from the bag can flow through the openings 210 in the tray 202 into the basin 204, and is collected in the basin 204.

The tray 202 is curved along its length towards a central channel 212 through the tray 202, as depicted in FIG. 5. As a result of the curved shape of the tray 202, fluid on the surface of the tray 202, such as fluid leaked from a fluid bag positioned on the tray 202, is directed by gravity towards the central channel 212 in the tray 202, and is drained into the basin 204 through the central channel 212. For example, the curved shape of the tray 202 causes fluid on the top surface of the tray between the openings 210 to be directed towards the central channel 212 and into the basin 204. As will be described in further detail herein, in some implementations, the basin 204 includes a leak detection sensor, and channeling fluid that has been leaked onto the tray 202 into the basin 204 through the openings 210 and the central channel 212 allows for leaks in a fluid bag placed on the tray 202 (e.g., drain bag 112) to be detected by the system 116.

Referring to FIGS. 5 and 6, the tray 202 defines handles 214, 216. The handles 214, 216 can be used to carry the tray 202 and to lift the tray 202 off of the basin 204 with ease, for example, during cleaning of the tray 202 and basin 204.

The tray 202 also includes conductive core elements 218, 220. The conductive core elements 218 220 extend through the tray 202 and are positioned on the tray 202 to contact a fluid bag (e.g., the dialysate bag 102 or the drain bag 112) positioned on the tray 202. The conductive core elements 218, 220 can interact with one or more heating elements in the basin 204 to heat fluid contained in the fluid bag positioned on the tray 202. For example, the dialysate bag 102 can be placed on the tray 202 prior to performing the fill, and heating of the conductive core elements 218, 220 by heating element(s) in the basin 204 can heat the dialysate contained in the bag, warming the dialysate fluid for use in the PD treatment.

Figure 7:
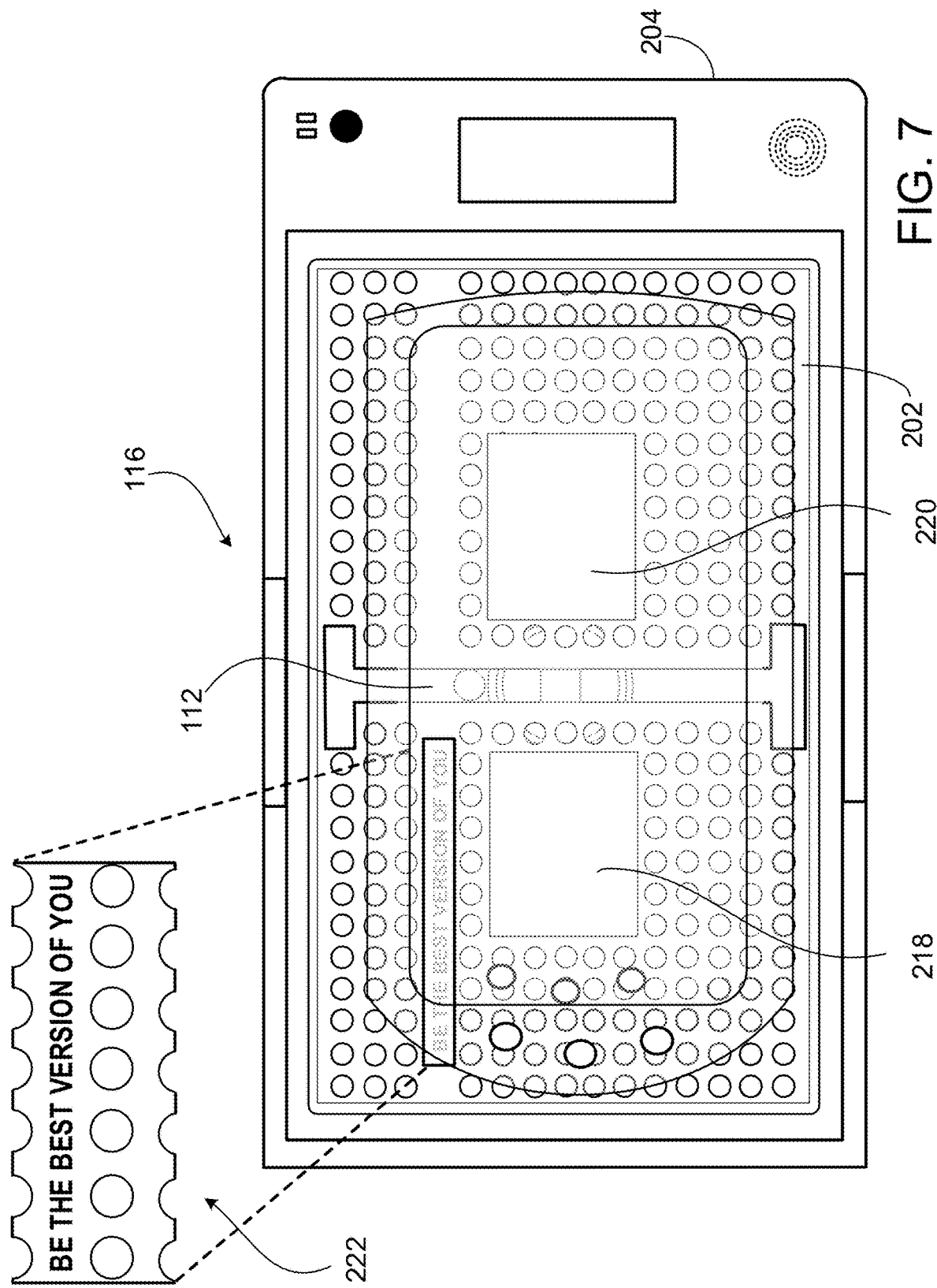
FIG. 7 is a top view of the basin system of FIG. 2 supporting a fluid bag of the PD system of FIG. 1.

As can be seen in FIGS. 6 and 7, the tray 202 includes contrast text 222 that allows a user of the basin system 116 to inspect the clarity of fluid contained within a fluid bag positioned on the tray 202. For example, referring to FIGS. 1 and 7, during a PD treatment, the drain bag 112 can be placed on the tray 202 and the clarity of effluent drained from the patient 110 into the drain bag 112 can be visually inspected by the patient 110 (or another user of the system 100) using the contrast text 222. For example, the patient 110 or another user of the system 100 can check the clarity of the effluent drained from the patient 110 into the drain bag 112 by determining whether the drained effluent is sufficiently clear such that the contrast text 222 on the tray 202 is visible through the effluent in the drain bag 112. If the contrast text 222 on the tray 202 is not visible through the effluent in the drain bag 112 due to cloudiness or discoloration of the effluent, this indicates that the patient 110 could be experiencing an infection, such as peritonitis. By checking the clarity of effluence drained from the patient 110 using the contrast text 222 on the tray 202, the patient 110 or another user of the system 100 is quickly and easily alerted of potential infections that the patient 110 may be experiencing and can seek appropriate medical attention for the patient 110. The contrast text 222 is printed on a surface of the tray 202 in a color that contrasts with the color of tray 202.

Figure 8:
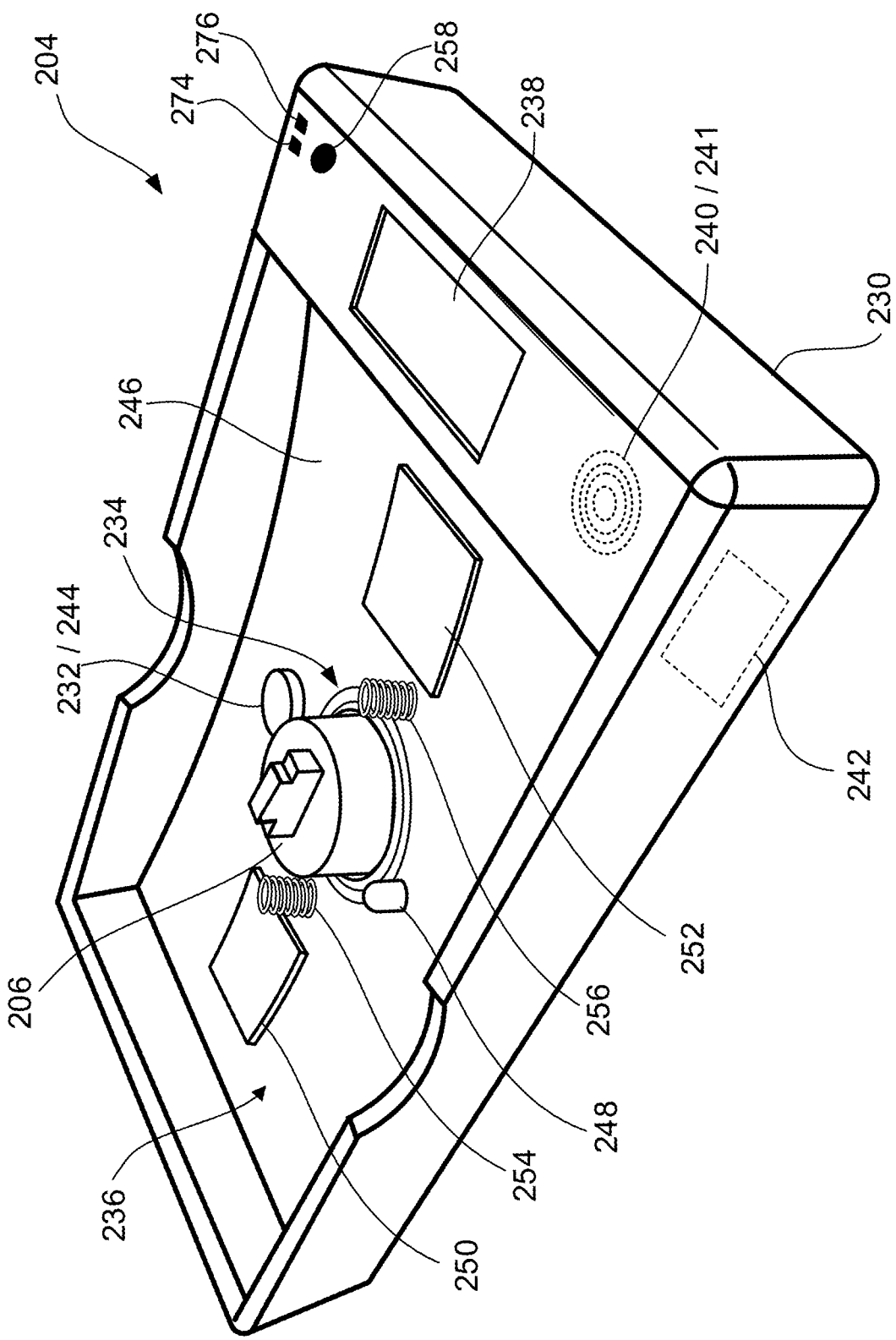
FIG. 8 is a perspective view of a basin of the basin system of FIG. 2.

FIG. 8 depicts the basin 204 of the basin system 116 of FIG. 1. The basin 204 is configured to cooperate with the tray 202 of the system 116 in order to support fluid bags (e.g., dialysate bags 102 or drain bags 112) placed on the tray 202 during PD treatment and collect any fluid leaking from the fluid bag placed on the tray 202. A control unit 242 (e.g., a microprocessor) of the basin 204 can be used to record, store, and wirelessly transmit one or more parameters related to the PD treatment.

Still referring to FIG. 8, the basin 204 includes a housing 230 that defines a chamber 236. The chamber 236 is configured to collect fluids leaked onto the tray 202 and into the basin 204. As depicted in FIG. 3, the tray 202 of the basin system 116 is positioned over the chamber 236 and the dialysate bag 102 or the drain bag 112 (depending on the phase of the PD treatment) is placed on top of the tray 202.

For example, during a dialysate heating step prior to the fill phase, the dialysate bag 102 is positioned on the tray 202 and the dialysate in the dialysate bag 102 is heated before being delivered to the patient. If the dialysate bag 102 includes a leak while positioned of the tray 202 for heating, dialysate will flow out of the dialysate bag 102, through the openings 210 and central channel 212 of the tray 202, and into the chamber 236 of the basin 204. Once the dialysate in the dialysate bag 102 has been heated and no leaks from the bag 102 are detected, the dialysate bag 102 is removed from the tray 202 and is attached to stand 104 so that the dialysate can be provided to the patient via gravity during treatment.

During the draining phase of the PD treatment, the drain bag 112 is positioned on the tray 202 and effluent is drained from the patient 110 and flows into the drain bag 112. If the drain bag 112 includes a leak, effluent will flow out of the drain bag 112, through the openings 210 and central channel 212 of the tray 202, and into the chamber 236 of the basin 204.

Figure 9:
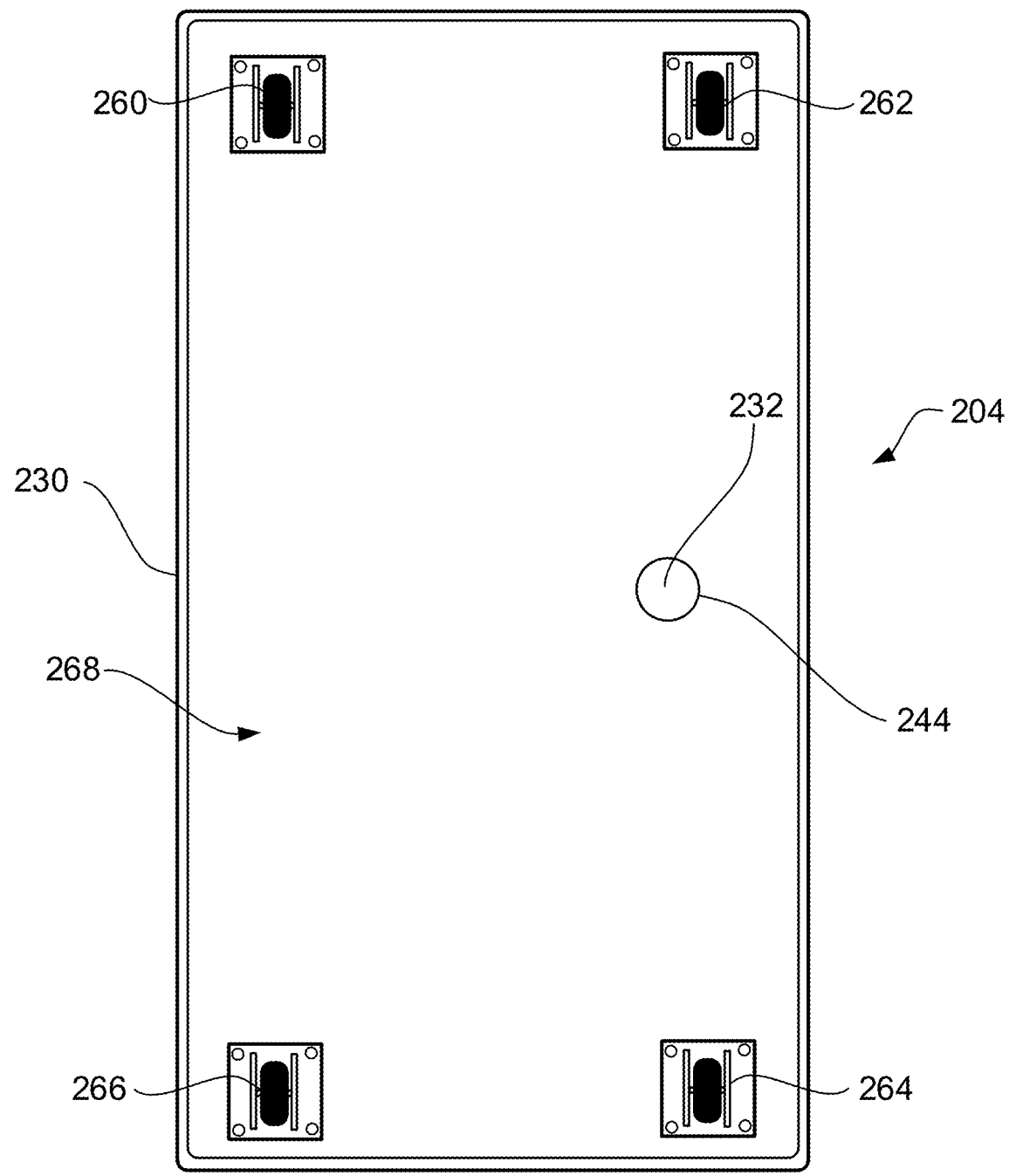
FIG. 9 is a bottom view of the basin of FIG. 8.

Referring to FIGS. 8 and 9, the housing 230 of the basin 204 further defines a drain opening 244 that extends through the housing 230. An expandable plug 232 can be inserted into the drain opening 244 in order to seal the drain opening 244 and prevent fluid from flowing out of the chamber 236 through the drain opening 244. For example, during the PD treatment, the expandable plug 232 can be disposed in the drain opening 244 to prevent any fluid leaked from a fluid bag positioned on the tray 202 from flowing out of the chamber 236 of the basin 204. The expandable plug 232 can be removed in order to drain fluid from the chamber 236 of the basin 204, for example, in order to clean the basin 204. Fluid collected in the chamber 236 is drained by positioning the basin 204 over a toilet, bathtub, or sink, and removing the expandable plug 232 from the drain opening 244 to allow the fluid in the chamber 236 to flow through the drain opening 244 into the toilet, bathtub, or sink.

Figure 10:
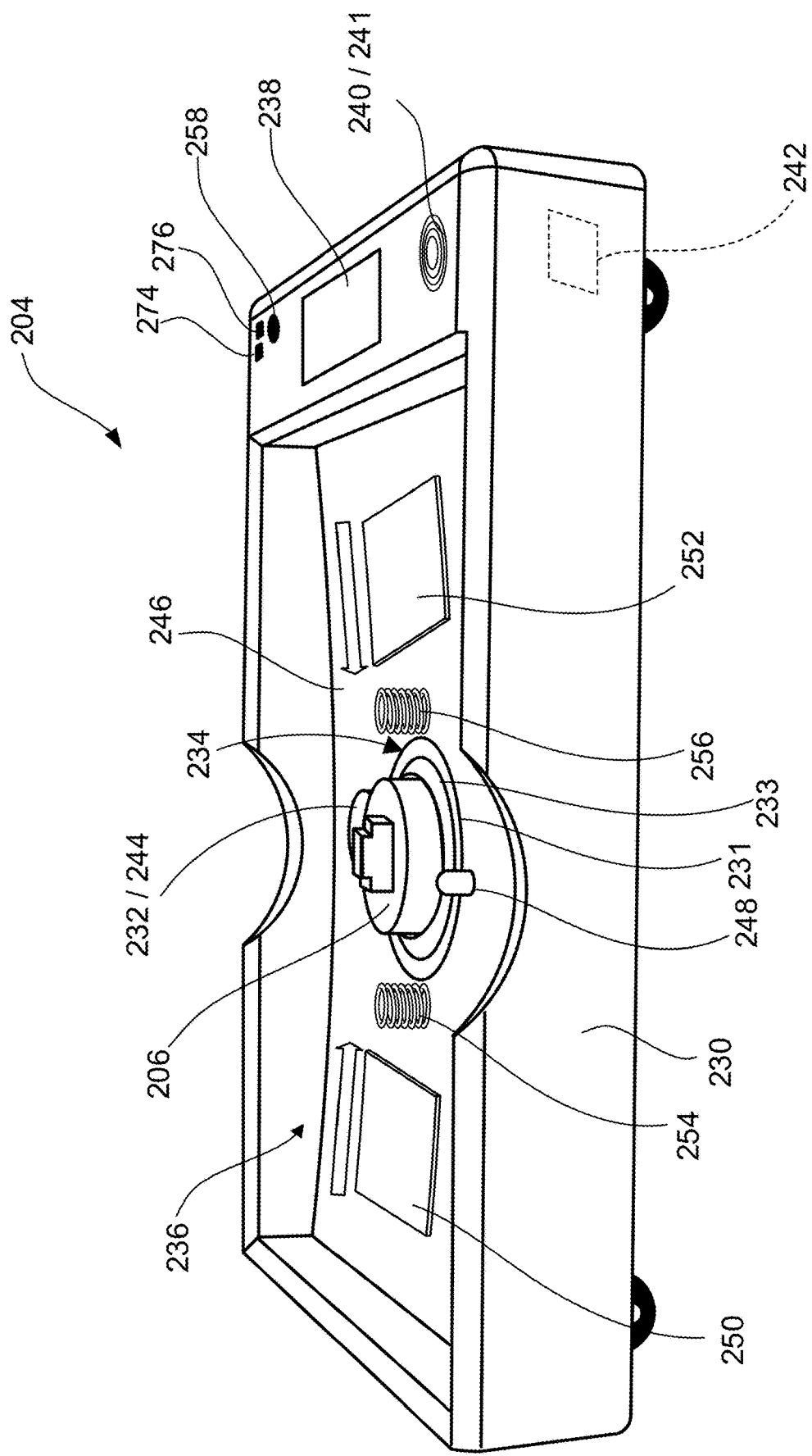
FIG. 10 is an elevated, side view of the basin of FIG. 8.

As depicted in FIG. 10, the bottom surface 246 of the chamber 236 slopes inwards towards the drain opening 244 in the chamber 236 to direct fluid leaked into the chamber 236 towards to drain opening 244. By directing fluid in the chamber 236 towards the drain opening 244, the curved bottom surface 246 of the chamber 236 allows for improved ease in draining fluid out of the chamber 236. In some implementations, the bottom surface 246 of the chamber 236 is clear in order to allow a user to more easily inspect the color and clarity of effluent contained in a drain bag 112 positioned over the basin 204 (e.g., via a tray 202 coupled to the basin 204).

The basin 204 also includes a leak detector 234 for detecting fluid that has leaked into the basin 204. The leak detector 234 is positioned within the chamber 236 and includes a wetness sensor configured to detect when a fluid contacts the leak detector 234. For example, if the fluid bag (e.g., the dialysate bag 102 or the drain bag 112) positioned on the tray 202 leaks fluid (e.g., dialysate or effluent) onto the tray 202, into the chamber 236 of the basin 204, and into contact with the leak detector 234 in the chamber 236, the leaked fluid will be automatically detected by the leak detector 234.

The leak detector 234 is formed of conductive (e.g., metal) material that is configured to detect whenever a fluid, such as leaked dialysate or effluent, contacts the leak detector 234. For example, as can be seen in FIGS. 8 and 10, in some implementations, the leak detector 234 is formed as two concentric metal rings 213, 233 that are positioned within a channel formed between the scale 205 and the bottom surface 246 of the chamber 236, with a first ring 231 serving as a positive terminal and a second ring 233 serving as a negative terminal. In addition, the bottom surface 246 of the chamber 236 is sloped to direct fluids leaked into the chamber 236 via gravity towards the leak detector 234. Positioning the leak detector 234 within the chamber 236 such that the sloped bottom surface 246 of the chamber 236 directs fluid leaked from a fluid bag towards the leak detector 234 allows for prompt detection of any leaks in the fluid bag supported by the system 116.

When electrically conductive fluid, such as dialysate or effluent, leaks into the chamber 236 and contacts the two metal rings 231, 233 of the leak detector 234, the leaked fluid bridges the gap between the metal rings 231, 233 and allows electrical current to flow from positive to negative terminals to complete a circuit. In response to completion of the circuit formed by the leak detector, the leak detector 234 can generate a signal indicating that wetness has been detected in the basin 204 and transmit the signal to a computing device. For example, the leak detector 234 can be configured to transmit a signal to the control unit 242 of the basin 204 in response to fluid contacting the leak detector 234. In response to receiving a signal from the leak detector 234 indicating a leak, the control unit 242 can generate an alert indicating that a leak in the fluid bag on the tray 202 has been detected by the system 116. In response to the control unit 242 receiving a signal from the leak detector 234 indicating the presence of a fluid leak, the control unit 242 can control a graphical display 238 on the basin 204 to display a message or warning indicating that a fluid leak from the fluid bag has been detected by the system 116. The control unit 242 can alternatively or additionally control a speaker 240 of the basin 204 to emit an audible alert indicating that a fluid leak has been detected by the system 116.

Referring back to FIGS. 2 and 8, the basin 204 also includes a weight scale 206 configured to measure the weight of fluid contained in a fluid bag (e.g., the dialysate bag 102 or the drain bag 112) positioned on the tray 202 of the basin system 116. The weight scale 206 can include a load cell configured to measure the force applied onto the weight scale 206 by the tray 202 positioned on the weight scale 206 together with any objects positioned on the tray 202, such as the drain bag 112 or the dialysate bag 102.

The weight scale 206 is communicably coupled to the control unit 242 of the basin 204 and is configured to transmit signals to the control unit 242 indicating a weight detected by the weight scale 206. For example, in order to determine an amount of fluid drained from the patient 110 during the drain phase of a PD treatment cycle, an empty drain bag 112 can be placed on the tray 202, and the weight scale 206 can detect an incremental increase in weight applied to the weight scale 206 corresponding to a predetermined initial weight indicating that an empty drain bag 112 has been placed on the tray 202. The weight corresponding to an empty drain bag 112 can be recorded and stored by the control unit 242 of the basin 204. In response to the scale 206 detecting a weight indicating that an empty drain bag 112 has been placed on the tray 202, the weight scale 206 can send a signal to the control unit 242 indicating the start time of the drain phase of the cycle and can begin measuring the weight of the tray and drain bag 112 as the drain phase proceeds.

Once the drain phase has ended, and thus no additional fluid has been added to the drain bag 112 for a predetermined amount of time, the weight scale 206 can detect that a predetermined amount of time has elapsed since any weight increases were detected by the scale 206 and, in response, can send a signal to the control unit 242 indicating an end time of the drain phase of the treatment cycle.

Based on the signals received from the weight scale 206, the control unit 242 can determine the length of the drain phase of the PD treatment cycle. For example, the control unit 242 can calculate the amount of time elapsed between the time that the weight scale 206 transmitted a signal indicating an initial weight for the drain phase and the time that the weight scale 206 transmitted a signal indicating a final weight for the drain phase in order to determine the duration of the drain phase.

The control unit 242 can also use the signals received from the weight scale 206 to determine a total amount of fluid drained from the patient 110 during the PD treatment cycle. For example, the control unit 242 can calculate the difference between the final weight measured by the weight scale 206 during the drain phase of the treatment cycle and the initial weight measured by the weight scale 206 at the beginning of the drain phase of the treatment to determine a total weight of effluent drained from the patient 110 and captured in the drain bag 112 during the drain phase of the cycle.

In addition, the weight scale 206 can be used to determine a volume of dialysate contained in a dialysate bag 102 used during the fill phase of the PD treatment cycle. For example, before the beginning the fill phase of treatment, a dialysate bag 102 can be positioned on the tray 202 in order to warm the dialysate in the bag 102, as will be described in further detail herein. As the dialysate bag 102 is being heated by the system 116, the weight of a dialysate bag 102 positioned on the tray 202 can be automatically detected by the weight scale 206 and a signal can be transmitted from the weight scale 206 to the control unit 242 of the basin 204 indicating the initial weight of the dialysate bag 102. Based on this weight detected by scale 206, the volume of dialysate fluid in dialysate bag 102 can be determined by the control unit 242. Once the dialysate in the dialysate bag 102 has been heated, the dialysate bag 102 is removed from the tray 202 and is attached to stand 104 so that the dialysate can be provided to the patient via gravity during treatment.

In some implementations, the system 116 is automatically turned on or awakened from a sleep mode in response to the weight scale 206 detecting a weight increase corresponding to either a full dialysate bag or an empty drain bag being placed on the tray 202.

Figure 13:
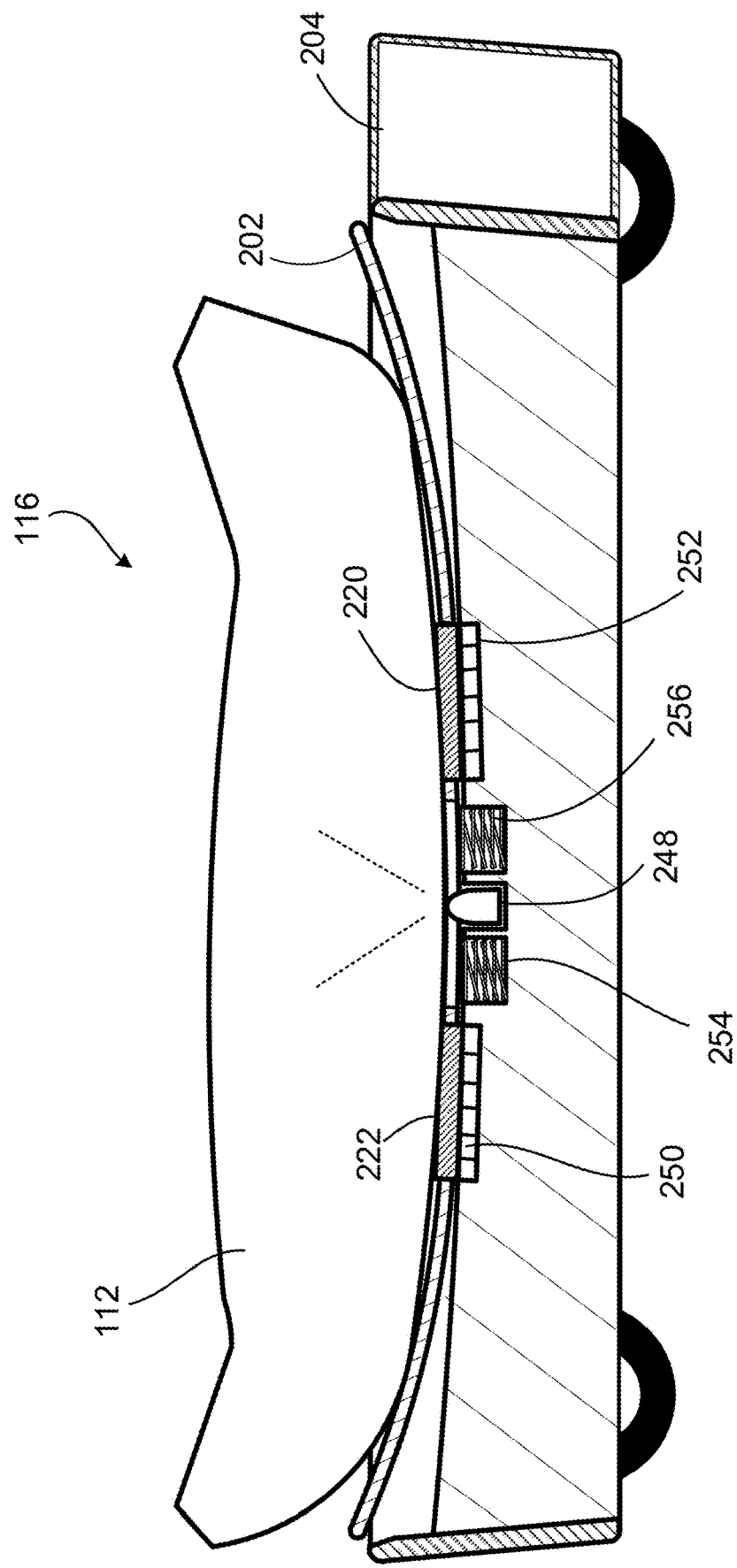

As depicted in FIGS. 8 and 13, the basin 204 includes an effluent sensor 248 configured to detect one or more characteristics of effluent contained in the drain bag 112 positioned on the tray 202 over the effluent sensor 248. In some implementations, the effluent sensor 248 is optical sensor that is configured to transmit and detect light in the visible and/or UV spectrums. For example, the effluent sensor 248 can be an optical sensor configured to detect various colors of the effluent in drain bag 112 corresponding to various conditions including, but not limited to hemoperitoneam, chylous effluent, bile in the effluent, duodenal ulcer perforation, large bowel perforation, dye in effluent (e.g., resulting from fluorescein angiography), an icodextrin reaction with iodine, methemalbumin pancreatitis, and intravenous administration of dextran and Rifampicin. The effluent sensor 248 can also be used to determine the clarity of effluent drained from the patient 110.

Referring to FIG. 13, during or at the end of the drain phase of a PD treatment cycle, the effluent sensor 248 can be operated to determine the color and clarity of effluent contained in a drain bag 112 positioned on the tray 202 of the system 116. In some cases, the effluent sensor 248 is controlled to scan the effluent in response to a user command to activate the effluent sensor 248 that is received through a graphical display 238 or a microphone 241 of the basin 204.

The effluent sensor 248 is communicably coupled to the control unit 242 of the basin 204 and is configured to transmit a signal to the control unit 242 indicating one or more characteristics of effluent drained from the patient. For example, in response to the effluent sensor 248 scanning the effluent in the drain bag 112 positioned on the tray 202, the effluent sensor 248 can transmit a signal (e.g., wired or wirelessly) to the control unit 242 of the basin 204 indicating one or more characteristics of the effluent, such as clarity and color. In some implementations, the control unit 242 records the effluent characteristics received from the effluent sensor 248 in local data storage. In some implementations, the control unit 242 transmits the effluent characteristics received from the effluent sensor 248 to one or more remote computing devices, such as remote data storage devices.

In some implementations, when the effluent sensor 248 has completed the scan of the drain bag 112, the control unit 242 controls the graphical display 238 to display a message indicating the results of the effluent scan. In some implementations, when the effluent sensor 248 has completed the scan of the drain bag 112, the control unit 242 controls the speakers to emit an audible message indicating the results of the effluent scan. By automatically monitoring effluent conditions using an effluent sensor 248 and notifying the patient or another user of the results of the effluent scan, patient safety can be improved through early detection of signs of infection.

As can be seen in FIG. 8, the basin 204 also includes one or more heating elements 250, 252. The heating elements 250, 252 can be used to heat fluid contained in a fluid bag positioned on the tray 202 of the system 116. For example, before performing the fill phase of a PD treatment cycle, the fresh dialysate fluid in dialysate bag 102 is warmed to a predetermined temperature. In order to accomplish this pretreatment warming, a dialysate bag 102 can be placed on the tray 202 of the system 116, and the heating elements 250, 252 in the basin can transfer heat to the dialysate bag 102, heating the dialysate fluid contained in the dialysate bag 102.

The heating elements 250, 252 can be controlled by the control unit 242 to provide heat at a particular temperature. For example, the control unit 242 can control the heating elements 250, 252 to heat to a predetermined temperature for a predetermined amount of time. In some implementations, a user can input a temperature (e.g., using the graphical display 238 or the microphone 241 of the basin 204), and the control unit 242 controls the heating elements 250, 252 to heat to the user-specified temperature.

The basin system 116 can alert a user once the predetermined or user-specified temperature has been reached. For example, in some implementations, the system 116 includes temperature sensors (e.g., one or more thermistors) in contact with the dialysate bag 102, such as temperature sensors positioned on tray 202 that detect the temperature of the fluid in dialysate bag 102 and transmit signals indicating the temperature of the dialysate to the control unit 242. In response to receiving a signal from one or more temperature sensors indicating that the fluid in the dialysate bag 102 has reached the predetermined or user-specified temperature, the control unit 242 of the basin 204 can cause a visual alert to be displayed on the graphical display 238 or can cause the speakers 240 to emit an audible alert indicating that the dialysate in the bag 102 has been heated to the predetermined or user-specified temperature.

Figure 11:
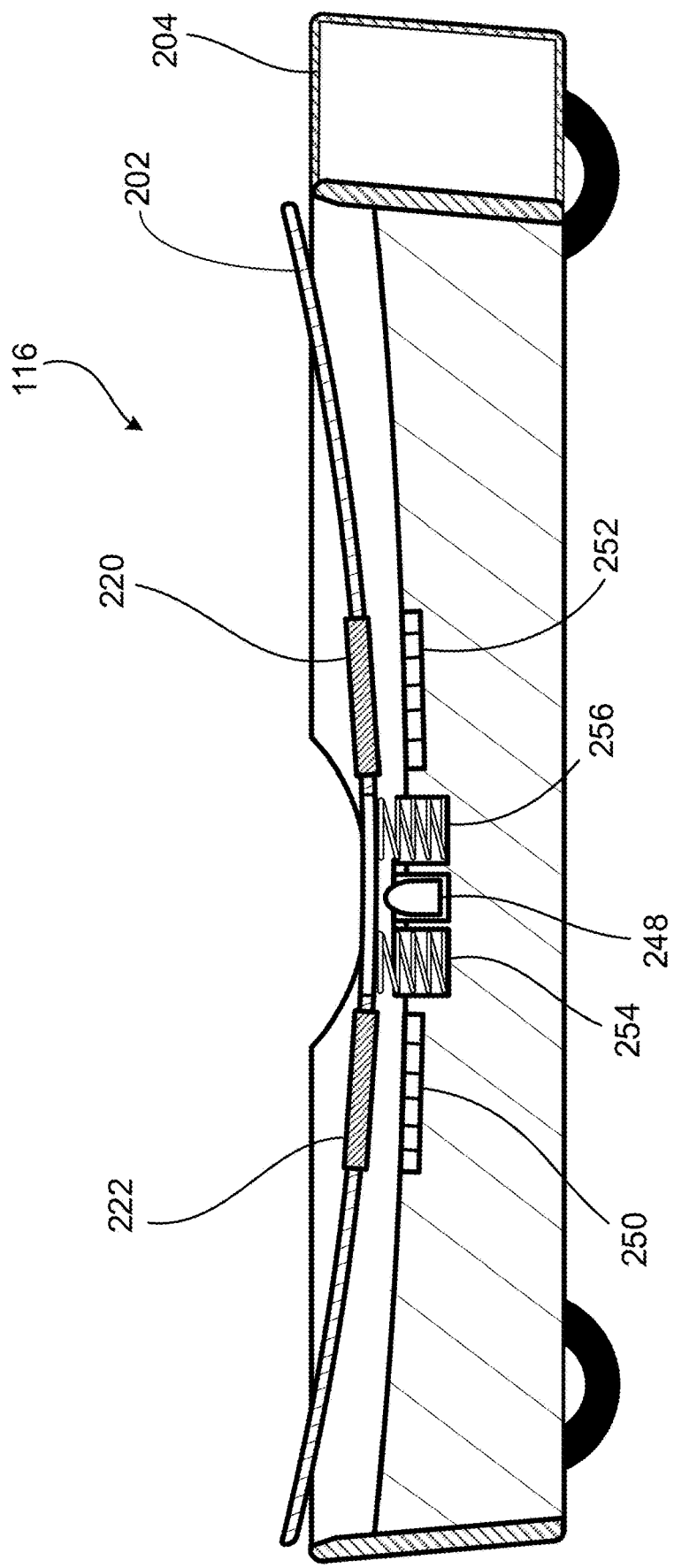
FIG. 11 is a schematic cross-section view of the basin system of FIG. 2.
Figure 12:
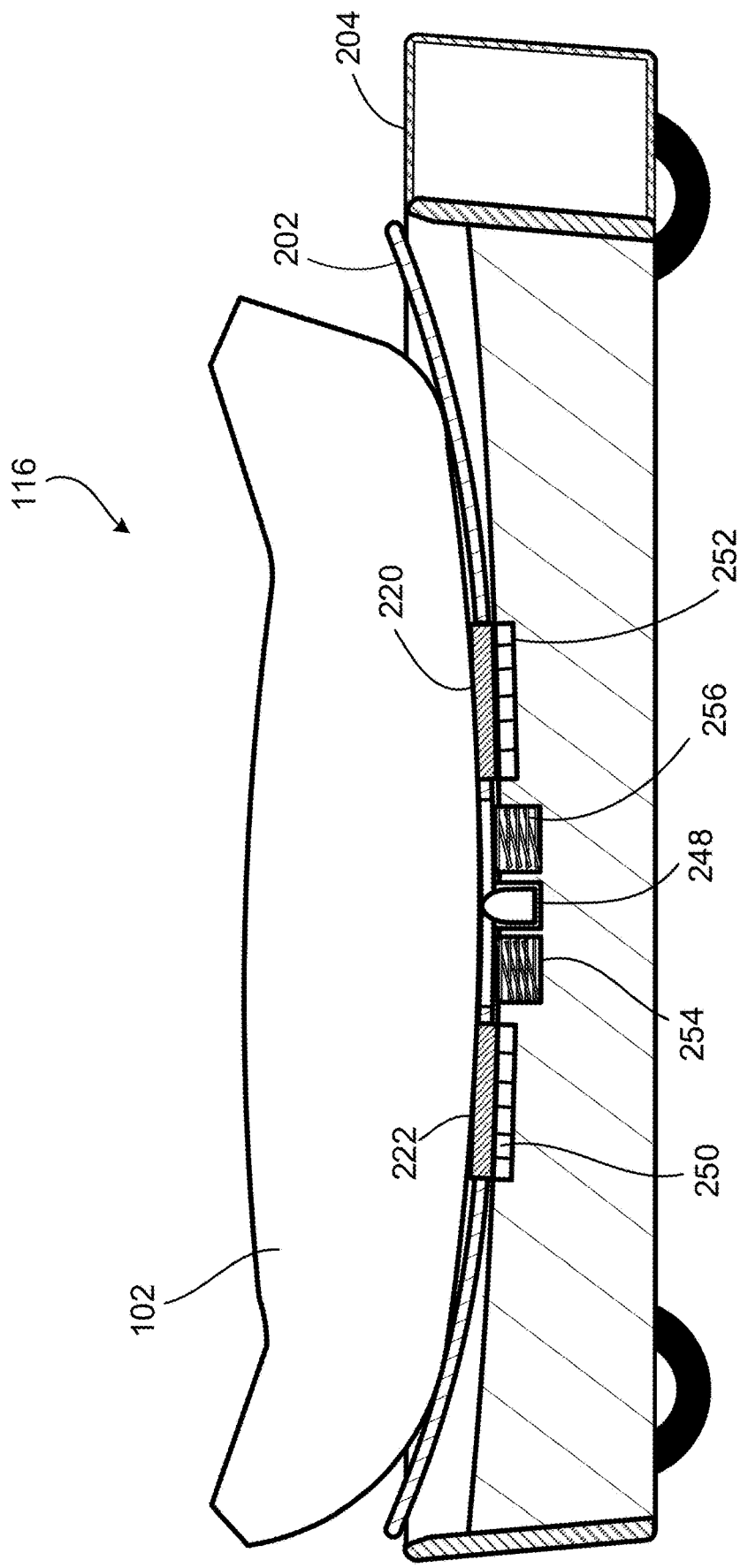
FIGS. 12 and 13 are schematic cross-section views of the basin system of FIG. 2 supporting fluid bags of the PD system of FIG. 1.

The heating elements 250, 252 are configured to contact and heat the conductive core elements 218, 220 extending through the tray 202, which in turn heat a fluid contained inside a fluid bag positioned on the tray 202. FIGS. 11 and 12 depict schematic cross-sectional views of the basin system 116 showing the interaction of the heating elements 250, 252 in the basin 204 with the conductive core elements 218, 220 of the tray 202. As can be seen in FIGS. 11 and 12, when the tray 202 is positioned over and coupled to the basin 204, the conductive core elements 218, 220 are aligned with and positioned over the heating elements 250, 252 of the basin 204. Contact between the conductive core elements 218, 220 and the heating elements 250, 252 when the heating elements 250, 252 are activated causes the temperature of the conductive core elements 218, 220 to rise, which heats the fluid contained in any fluid bag positioned on the tray 202.

The basin includes depressible members 254, 256 to control contact between the conductive core elements 218, 220 and the heating elements 250, 252. The depressible members 254, 256 can include, but are not limited to, coil springs, leaf springs, wave springs, or torsion springs. The depressible members 254, 256 are positioned within the chamber 236 of the basin 204 and contact the tray 202 when the tray 202 is positioned over and coupled to the basin 204. As can be seen in FIG. 11, when the tray 202 is empty or is supporting a small amount of weight, such as an empty fluid bag, the depressible members 254, 256 remain in an expanded configuration, which prevents the conductive core elements 218, 220 from contacting the heating elements 250, 252 in the basin 204. When a threshold amount force is applied to the tray 202, the depressible members 254, 256 are compressed (as depicted in FIG. 12), which causes the conductive core elements 218, 220 to come into contact with the heating elements 250, 252 in the basin 204. Whenever the heating elements 250, 252 are activated, contact between the conductive core elements 218, 220 and the heating elements 250, 252, as shown in FIG. 12, heats the conductive core elements 218, 220. In some implementations, the threshold amount of force required to compress the depressible members 254, 256 corresponds to the force applied by a full or nearly full fluid bag positioned on the tray 202 (e.g., dialysate bag 102 in FIG. 12).

Once a threshold amount of force applied to the tray 202 is removed, the depressible members 254, 256 return to their expanded state causing the conductive core elements 218, 220 to no longer contact the heating elements 250, 252. For example, by removing a dialysate bag 102 from the tray 202, depressible members 254, 256 return to their expanded state and separate the conductive core elements 218, 220 from the heating elements 250, 252, as depicted in FIG. 11. By preventing the conductive core elements 218, 220 in the tray 202 from contacting the heating elements 250, 252 when the tray 202 is empty, fluid bags can be safely heated with a reduced risk of injury (e.g., burns) to the users of the system 116.

For example, when a fresh dialysate bag 102 is placed on the tray 202, the depressible members 254, 256 are compressed and the conductive core elements 218, 220 contact the heating elements 250, 252, causing the heating elements 250, 252 to heat the conductive core elements 218, 220 when the heating elements 250, 252 are activated. As the heating elements 250, 252 heat the conductive core elements 218, 220, heat is transferred from the conductive core elements 218, 220 to the dialysate in the dialysate bag 102, heating the dialysate. Once the dialysate bag 102 has been heated to the desired temperature for treatment, the dialysate bag 102 is removed from the tray 202, which causes the depressible members 254, 256 return to their expanded state (as depicted in FIG. 11) and, as a result, raises the conductive core elements 218, 220 out of contact with the heating elements 250, 252.

In addition, in some implementations, the heating elements 250, 252 are automatically deactivated when a force above a threshold force is no longer being applied to the tray 202. For example, when a dialysate bag 102 has been heated and is removed from the tray 202, as depicted in FIG. 11, the weight scale 206 detects the reduction in weight caused by the removal of the dialysate bag 102 and transmits a signal to the control unit 242 indicating the updated, reduced weight. In response to receiving the signal from the weight scale 206 indicating the reduced weight, the control unit 242 deactivates the heating elements 250, 252. By deactivating the heating elements 250, 252 in response to the fluid bag being removed from the tray 202, fluid bags can be safely heated with reduced risk of injury (e.g., burns) to the user of the system 116.

The heating elements 250, 252 in the basin 204 can be induction heating elements that comprise an induction coil. For example, the induction coil of the heating elements 250, 252 can generate a magnetic field that is passed onto the conductive core elements 218, 220 when the conductive core elements 218, 220 are in contact with the heating elements 250, 252, which in turn heats the conductive core elements 218, 220. By using induction heating elements 250, 252, the conductive core elements 218, 220 are only heated above room temperature when in contact with the heating elements 250, 252 and the rest of the system 116, including the heating elements 250, 252, remain at room temperature during the heating process. As such, fluid bags can be quickly and safely heated with reduced risk of injury (e.g., burns) to the user of the system 116.

The basin 204 also includes one or more light emitting diodes (LEDs) 258 to indicate when a fluid bag is being heated by the system 116. For example, when a fluid bag (such as dialysate bag 102) is positioned in the tray 202 (as determined based on signals transmitted by weight scale 206) and the heating elements 250, 252 are activated, one or more LEDs 258 on the basin 204 are illuminated to indicate that the fluid bag is being heated by the basin 204. Once the fluid bag is removed from the tray 202, as determined based on a decrease in weight measured by the weight scale 206, or once the heating elements 250, 252 are deactivated, the LED(s) 258 are turned off.

Referring back to FIG. 9, the basin 204 includes wheels 260, 262, 264, 266 that allow for easy movement of the system 116. Each wheel is coupled to the bottom surface 268 of the basin 204 proximate a respective corner of the basin 204. The wheels 260, 262, 264, 266 can be full-swivel wheels. In some cases, one or more of the wheels 260, 262, 264, 266 include a locking caster that can be engaged to lock the respective wheels 260, 262, 264, 266 and temporarily prevent movement of the basin 204 (e.g., during treatment).

Figure 14:
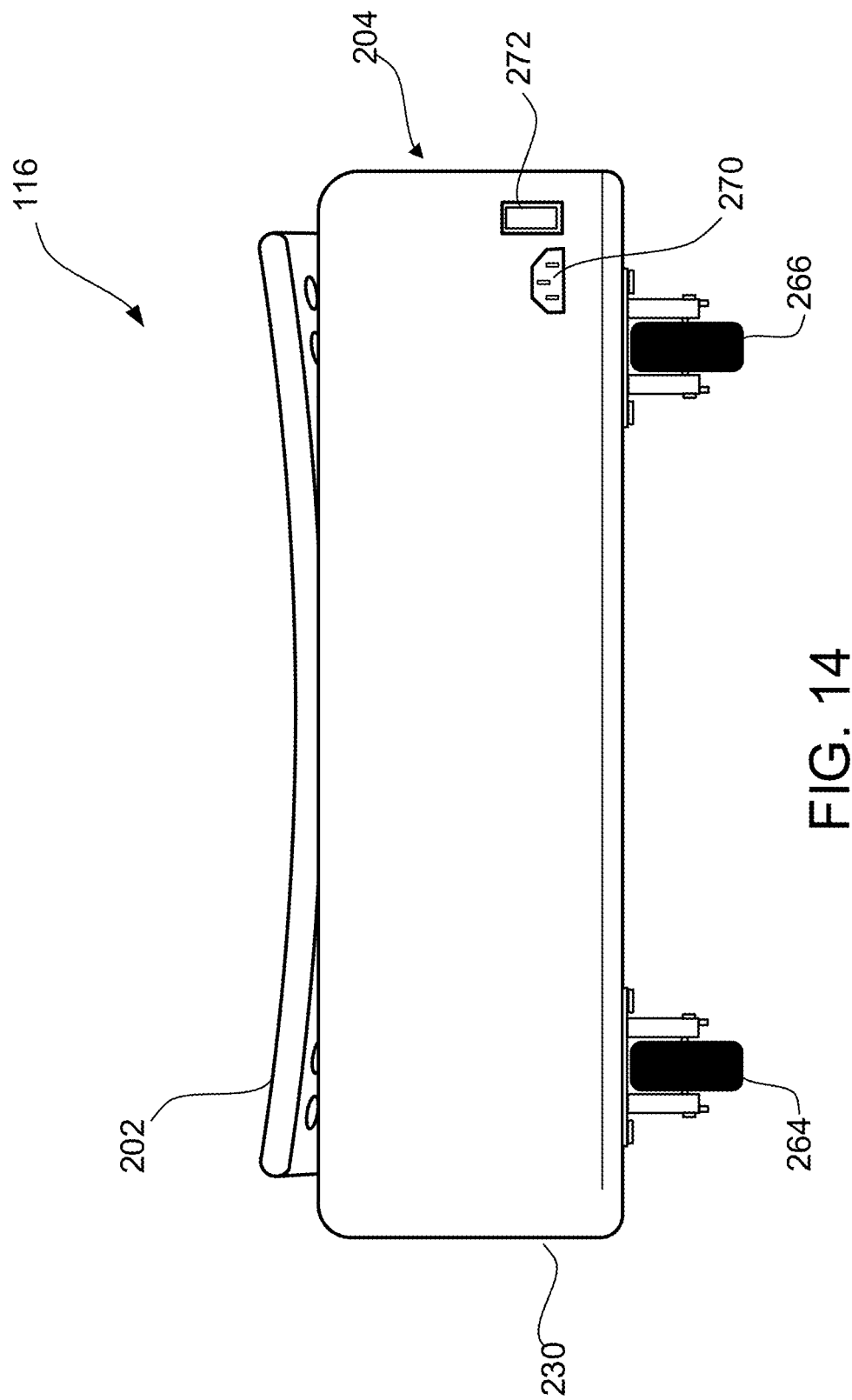
FIG. 14 is a rear view of the basin system of FIG. 2.

Referring to FIG. 14, the basin 204 includes a power adapter 270 that can be used to connect the basin 204 a power supply in order to provide power to one or more components of the basin 204. The basin 204 can include a rechargeable battery that is used to power various components of the basin 204, such as the weight scale 206, the effluent sensor 248, and the control unit 242. The battery can be charged by connecting the power adapter 270 to a power supply (e.g., using a cable). In some implementations, the power adapter 270 is a 60 Watt power adaptor. The basin 204 also includes a switch 272 for turning the electronic components of the basin 204 on and off.

As can be seen in FIG. 8, the basin 204 also includes ports 274, 276 configured to couple to electronic devices. For example, the ports 274, 276 can be configured to interface with a portable memory device, such as a universal serial bus (USB) storage device or other flash memory card, to store one or more treatment parameters captured by the system 116 onto the storage device. For example, the control unit 242 can transmit one or more treatment parameters received and recorded by the control unit 242 to a portable memory device coupled to one of the ports 274, 276 on the basin 204. In some implementations, the control unit 242 is configured to generate a treatment report containing all treatment parameters for the most recent PD treatment performed using the system, and export the treatment report onto a portable memory device coupled to one of the ports 274, 276 on the basin 204.

Referring to FIG. 1, the PD system 100 includes a flow sensor 120 that is configured to measure the fluid flowing from the dialysate bag 102 into the patient's peritoneal cavity during the fill phase of the treatment cycle. The flow sensor 120 can be coupled to the fluid line 106 between the dialysate bag 102 and the transfer set 108 to measure fluid flow along the fluid line 106. The flow sensor 120 detects and records a time when flow through the fluid line 106 is first sensed (corresponding to the start time of the fill phase) and a time when flow along the fluid line 106 stops (corresponding to the end time of the fill phase). During the fill phase, the flow sensor 120 measures the amount of dialysate fluid that is provided to the patient 110 during the fill phase via fluid line 106.

At the end of the fill phase of the PD treatment, a user can connect the flow sensor 120 to a port 274, 276 on the basin 204, and the flow data captured by the flow sensor 120 can be transmitted to the control unit 242 of the basin 204. Based on the data provided by the flow sensor 120, the control unit 242 can determine various parameters for the fill phase of the treatment, including a fill start time, a fill end time, an amount time elapsed during the fill phase, and an amount (e.g., volume) of fill fluid provided to the patient 110 during the fill phase. In some implementations, the control unit 242 transmits the treatment data determined based on the data received from the flow sensor 120 to one or more remote computing devices.

In some implementations, the control unit 242 can compare the data regarding fill volume received from the flow sensor 120 during the fill phase with data indicating an amount drained from the patient during the drain phase (e.g., based on data received from weight scale 206) to determine ultrafiltration efficacy for the treatment cycle. For example, the difference between the fill volume measured by the flow sensor and the amount of fluid drained from the based determined based on data received from the weight scale 206 indicates the additional amount of fluid drained from the patient during the drain phase, which can be used to analyze the ultrafiltration efficiency of the treatment.

In some implementations, the control unit 242 determines an end time for the fill phase of the cycle based on the received flow sensor 120 data, and, based on the fill phase end time, the basin 204 generates an alert after a predetermined amount of time has elapsed from the fill end time indicating to a user that the dwell period is complete. For example, after a predetermined amount of time corresponding to the dwell time has elapsed from the fill phase end time, the control unit 242 can control the graphical display 238 to display an alert indicating that the dwell phase is complete and the drain phase can begin. In some implementations, after a predetermined amount of time corresponding to the dwell time has elapsed from the fill phase end time, the control unit 242 can control the speaker 240 to emit an audible alert indicating that the dwell phase is complete and the drain phase can begin.

The control unit 242 can utilize the data received from the flow sensor 120 and the weight scale 206 to determine a dwell time performed during the treatment cycle. For example, the end time for the fill cycle can be determined based on data indicating the time that the flow sensor 120 stopped detecting flow along the fluid line 106 between the dialysate bag 102 and transfer set 108. Similarly, the start time of the drain cycle can be determined based on the first weight increase above a threshold amount recorded by the weight scale 206 after the end of the fill phase. The control unit 242 can then determine the total dwell time based on the time elapsed between the fill phase end time and the drain phase start time determined from the data received from the flow sensor 120 and the weight scale 206.

As previously discussed, the graphical display 238 (shown in FIG. 8) can be configured to display messages to a user of the basin system 116, such as alarms and warning messages. In some implementations, the control unit 242 controls the graphical display 238 to display messages and alerts in response to the control unit 242 receiving signals from one or more sensing elements of the basin 204, such as the leak detector 234, the weight scale 206, or the effluent sensor 248.

The graphical display 238 can be a touchscreen display and can be used to display a graphical user interface. A user can interact with the graphical user interface displayed on the graphical display 238 to control the operation of one or more components of the basin 204, such as controlling the weight scale 206 to take a weight measurement or controlling the effluent sensor 248 to analyze effluent contained in a drain bag 112 positioned on the tray 202.

In addition, a user can use the graphical user interface displayed on the graphical display 238 to enter data related to the PD treatment, such as the clarity of the effluent drained from the patient during the drain phase, the concentration of the dialysate fluid used for the fill phase, the start time of the fill phase, the end time of the fill phase, the expiry date of the dialysate used for the fill phase, the volume of dialysate to be provided to the patient during the fill phase, clarity of the dialysate used for the fill phase. The treatment data input by the user using the graphical display 238 are received by the control unit 242 of the basin 204, and the control unit 242 can transmit the treatment data to one or more remote computing devices for storage and evaluation.

The graphical user interface displayed on the graphical display 238 can also be used to access treatment history. For example, a patient's previous treatment history can be displayed on the graphical display 238 of the basin 204. In some implementations, in response to a user's request for treatment history (e.g., input by the user using the graphical display 238), the control unit 242 communicates wirelessly with one or more remote storage devices to retrieve the patient's treatment history and controls the graphical display 238 to visually display the retrieved treatment history data. In some implementations, the patient's treatment history is encrypted, and a user must provide credentials in order to access the encrypted treatment data. For example, the user can provide credentials via a GUI displayed on the graphical display 238 or via voice control using microphone 241. The credentials required to retrieve encrypted treatment data can include a patient identification number, a password, a fingerprint, or retinal scan data.

The speaker 240 and microphone 241 of the basin can be used together to gather treatment data from a user of the system 116. For example, the speaker 240 can be controlled to audibly emit one or more questions regarding various treatment data, and the microphone 241 can be used to capture the user's response to each question emitted by the speaker 240. In some implementations, the speaker 240 is controlled to emit one or more treatment data questions in response to the control unit 242 receiving a signal from the weight scale 206 indicating a fluid bag (e.g., dialysate bag 102 or drain bag 112) has been placed on the tray 202.

The user input treatment parameters captured by the microphone 241 can be received by the control unit 242 and transmitted to one or more remote computing devices. For example, the speaker 240 of the basin 204 can be controlled to emit questions regarding the clarity of the effluent drained from the patient during the drain phase, the concentration of the dialysate used for the fill phase, the expiry date of the dialysate fluid used for the fill phase, the start time of the fill phase, the end time of the fill phase, the volume of dialysate to be provided to the patient during the fill phase, and the clarity of the dialysate used for the fill phase, and the user's response can be captured by the microphone 241 and processed by the control unit 242 of the basin 204.

In addition, a user can use the microphone 241 to provide audible instructions for controlling one or more elements of the basin 204, such as the weight scale 206, the heating elements 250, 252, and the effluent sensor 248. The user's audible instructions for controlling one or more components of the basin 204 can be captured by the microphone 241 and transmitted to the control unit 242, which controls the corresponding components of the basin 204 in response to the user's audible instructions. The use of the microphone 241 for capturing treatment data and user instructions is especially useful for users of the system 116 with visual impairments that prevent the user from being able to see and interact with a graphical display.

As previously discussed, the speaker 240 on the basin 204 can be used to audibly emit warnings or alarms generated by the control unit 242. Providing audible warnings and alarms using the speaker 240 in addition to or in lieu of visual warnings (e.g., displayed on graphical display 238) is particularly beneficial for users with visual impairments that prevent the users from seeing warnings displayed on a graphical display.

The control unit 242 (e.g., a microprocessor) of the basin 204 is connected to the weight scale 206, the leak detector 234, the effluent sensor 248, the heating elements 250, 252, the graphical display 238, the speaker 240, and the microphone 241 such that the control unit 242 can receive signals from and transmit signals to these components of the system in order to control operation of the basin 204 components and record treatment data. For example, in response to receiving one or more signals (e.g., from the weight scale 206 or the leak detector 234) the control unit 242 can control the graphical display 238 to a visual alert and/or control the speaker 240 to emit an audible alert.

The control unit 242 can receive treatment data from various sensors of the basin 204, including the weight scale 206, the leak detector 234, and the effluent sensor 248, as well as user-inputted data treatment received from the graphical display 238 and microphone 241. In some implementations, the control unit 242 automatically transmits the treatment data received from the sensors 206, 234, 248, the graphical display 238, and/or the microphone 241 to one or more remote computing devices. For example, the control unit 242 can transmit the received treatment data to a cloud computing device for storage. In some implementations, the control unit 242 transmits the received treatment data to one or more remote computing devices for display on the remote computing devices. For example, the control unit 242 can transmit the received treatment data to a mobile device of the patient for display on the patient's mobile device. In some examples, the control unit 242 transmits the received treatment data to a remote computing device operated by medical personnel assisting with the treatment for display at the remote computing device. In some implementations, the treatment data is wirelessly transmitted by the control unit 242 to one or more remote computing devices in real time.

In some implementations, the control unit 242 processes the received treatment data to generate a treatment report. The treatment report generated by the control unit 242 can include one or more of: drain start time, drain end time, the amount of fluid drained during the treatment, the clarity of effluent drained during the treatment, weight of the filled drain bag(s) 112 (e.g., as measured by weight scale 206), time elapsed between drain bag checks, dwell time, dialysate volume exchanged during treatment, dialysate temperature, fill start time, fill end time, initial treatment start time (e.g., for the day), final treatment end time (e.g., for the day), and a total number of cycles performed during the day. In some implementations, the treatment report generated by the control unit 242 is wirelessly transmitted to one or more remote computing devices. For example, the control unit 242 can be configured to automatically transmit the treatment report to one or more remote computing devices (e.g., remote storage devices and/or remote computing devices of medical personnel or patients) at a predetermined time each day. In some implementations, the control unit 242 stores the treatment report on a portable memory device (e.g., a USB device) coupled to a port 274, 276 of the basin.

Figure 15:
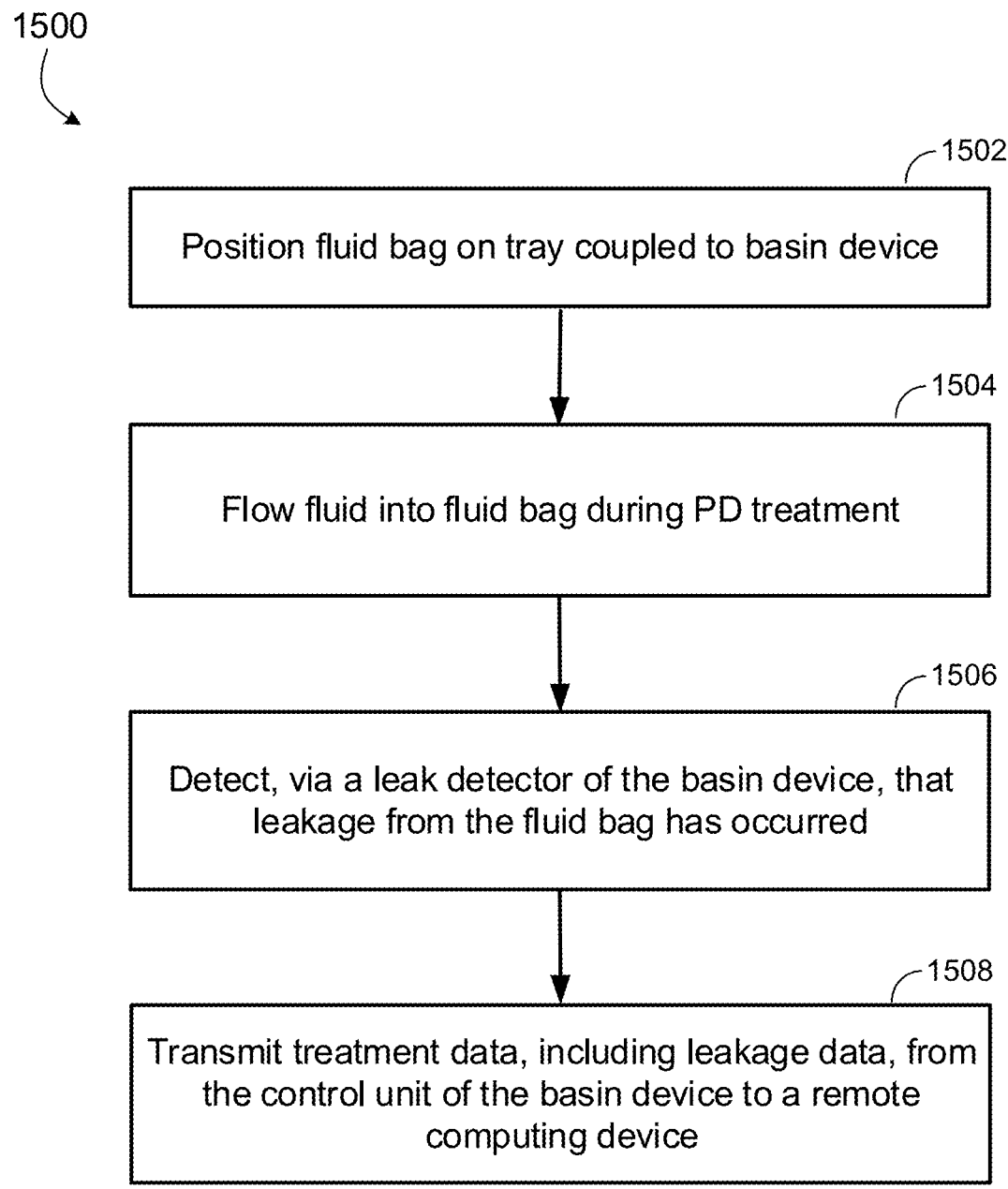
FIG. 15 is a flowchart showing a method of detecting a leak from a fluid bag supported by the basin system of FIG. 2.

FIG. 15 is a flowchart showing a method 1500 of detecting a fluid leak from a drain bag during PD treatment. Prior to performing the drain phase of a PD treatment cycle, a fluid bag (e.g., drain bag 112) is positioned on a tray (e.g., tray 202) coupled to a basin device (e.g., basin 204) (1502). The fluid bag is fluidly coupled to the patient's peritoneal cavity (e.g., using transfer set 108 and fluid line 114).

Once the fluid bag is positioned on the tray, effluent is flowed into the fluid bag during a PD treatment (1504). For example, fluid can be flow from the patient's peritoneal cavity into the fluid bag during a drain phase of the PD treatment. In some implementations, fluid is flowed into the fluid bag via gravity (e.g., as depicted in FIG. 1).

As discussed above, the tray includes markings (e.g., contrast text 222) and/or a sensor (e.g., effluent sensor 248) that can be used to determine the clarity of the fluid being flowed into the fluid bag. In some implementations, the basin includes a load cell (e.g., weight scale 206) to measure the weight of the fluid being flowed into the fluid bag.

If a leakage in the fluid bag occurs as fluid is flowed into the fluid bag positioned on the tray, a leak sensor coupled to a surface of the basin device (e.g., leak detector 234) detects the leakage (1506). For example, in some implementations, the tray supporting the fluid bag includes one or more openings (e.g., openings 210) or channels (e.g., central channel 212) to direct fluid leaked from the fluid bag on the tray into the basin. In some implementations, the tray has a curved profile to direct fluid leaked onto the tray towards a central channel in the tray (e.g., central channel 212) and into the basin. In some implementations, the leak detector is a wetness detector, and contact between the leaked fluid in the basin and the leak detector causes the leak detector to identify the leak and transmit a signal to a control unit (e.g., control unit 242) of the basin indicating the presence of a leak. In some implementations, the basin defines a chamber (e.g., chamber 236) to contain the leaked fluid and an inner surface of the basin (e.g., surface 246) is sloped to direct fluid contained in the basin towards the leak detector.

In response to receiving a signal from the leak detector indicating a leak has occurred, a control unit of the basin device (e.g., control unit 242) automatically transmits treatment data, including data indicating the occurrence of a fluid bag leak, to a remote computing device (1508). For example, the control unit can wirelessly transmit treatment data to one or more computing devices for storage or display of the treatment data at the one or more remote computing devices. In some implementations, treatment data received by the control unit, including the data received from the leak detector, is transmitted in real time from the control unit of the basin to the remote computing device. The treatment data transmitted from the control unit to the remote computing device can include one or more of: drain start time, drain end time, the amount of fluid drained during the treatment, the clarity of effluent drained during the treatment, weight of the filled drain bag(s) 112 (e.g., as measured by weight scale 206), time elapsed between drain bag checks, dwell time, dialysate volume exchanged during treatment, dialysate temperature, fill start time, fill end time, initial treatment start time (e.g., for the day), final treatment end time (e.g., for the day), and a total number of cycles performed during the day.

Figure 16:
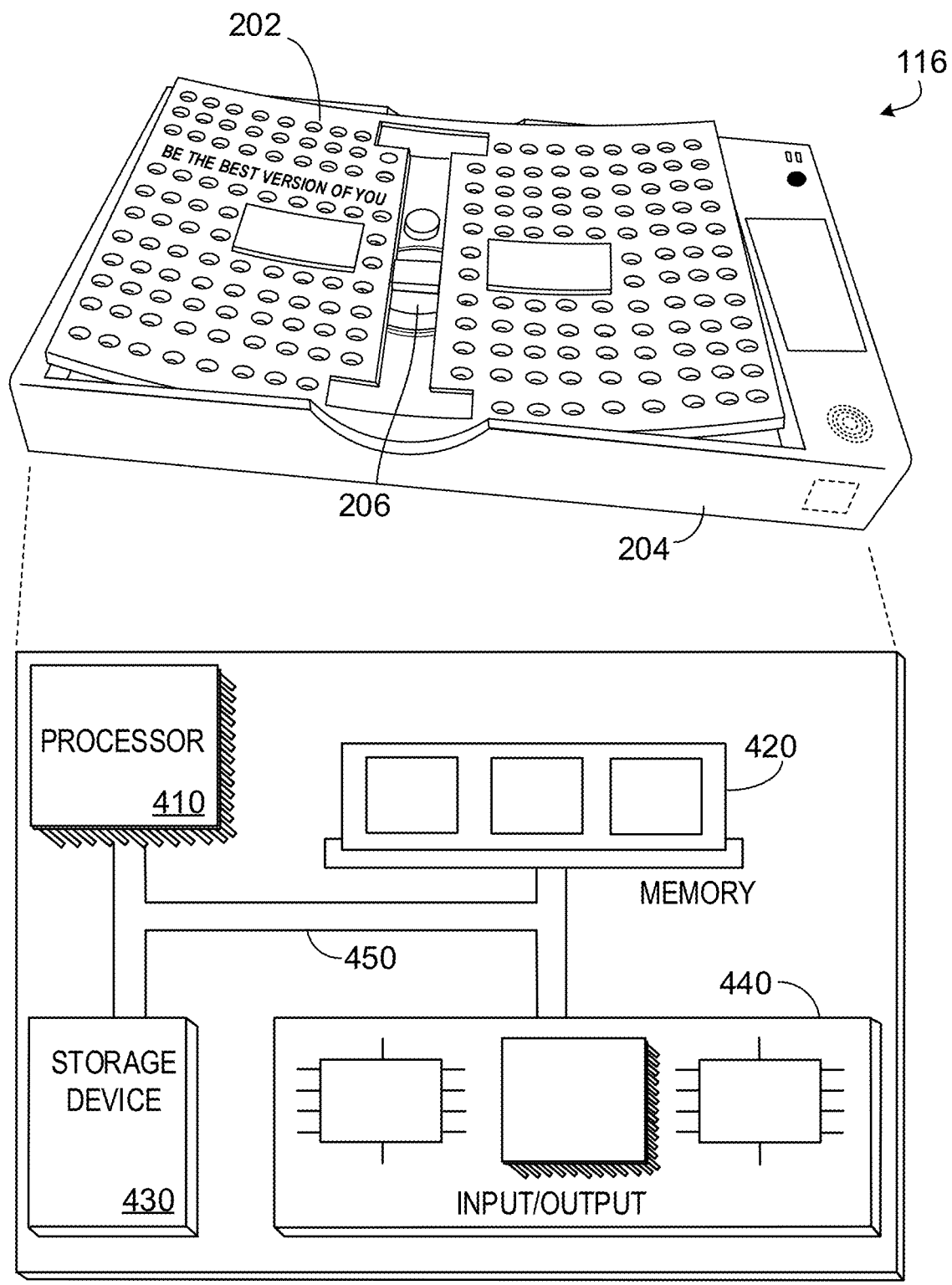
FIG. 16 is a block diagram of an example computer system by which a control unit of the basin system of FIG. 2 can be implemented.

FIG. 16 is a block diagram of an example computer system 400. For example, referring to FIG. 2, the control unit 242 of the basin system 116 could be an example of the system 400 described here. The system 400 includes a processor 410, a memory 420, a storage device 430, and an input/output interface 440. Each of the components 410, 420, 430, and 440 can be interconnected, for example, using a system bus 450. The processor 410 is capable of processing instructions for execution within the system 400. The processor 410 can be a single-threaded processor, a multi-threaded processor, or a quantum computer. The processor 410 is capable of processing instructions stored in the memory 420 or on the storage device 430. The processor 410 may execute operations such as receiving signals from a sensing element (e.g., the leak detector 234, the weight scale 206, and the effluent sensor 248 shown in FIG. 8) and transmitting the signal received from the sensing element to a remote computing device or storage device.

The memory 420 stores information within the system 400. In some implementations, the memory 420 is a computer-readable medium. The memory 420 can, for example, be a volatile memory unit or a non-volatile memory unit. In some implementations, the memory 420 stores a data structure. In some implementations, multiple data structures are used.

The storage device 430 is capable of providing mass storage for the system 400. In some implementations, the storage device 430 is a non-transitory computer-readable medium. The storage device 430 can include, for example, a hard disk device, an optical disk device, a solid-date drive, a flash drive, magnetic tape, or some other large capacity storage device. The storage device 430 may alternatively be a cloud storage device, e.g., a logical storage device including multiple physical storage devices distributed on a network and accessed using a network.

The input/output interface 440 provides input/output operations for the system 400. In some implementations, the input/output interface 440 includes one or more of network interface devices (e.g., an Ethernet card), a serial communication device (e.g., an RS-232 10 port), and/or a wireless interface device (e.g., an 802.11 card, a 3G wireless modem, a 4G wireless modem, a 5G wireless modem, or better). In some implementations, the input/output device includes driver devices configured to receive input data and send output data to other input/output devices, e.g., keyboard, printer and display devices 138. In some implementations, mobile computing devices, mobile communication devices, and other devices are used.

In some implementations, the system 400 is a microcontroller. A microcontroller is a device that contains multiple elements of a computer system in a single electronics package. For example, the single electronics package could contain the processor 410, the memory 420, the storage device 430, and input/output interfaces 440.

Although an example processing system has been described in FIG. 16, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disksand CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

A number of embodiments have been described. Nevertheless, it will be understood that various modifications may be made without departing from the spirit and scope of the disclosure.

For example, while the basin system 116 has been described as being used during a CAPD treatment, the basin system 116 can also be used during automated peritoneal dialysis (APD) treatments. During APD treatment, automated PD machines called PD cyclers control the entire PD process so that it can be performed at home usually overnight without clinical staff in attendance. Many PD cyclers are designed to automatically infuse, dwell, and drain dialysate to and from the patient's peritoneal cavity. APD treatment typically lasts for several hours, often beginning with an initial drain cycle to empty the peritoneal cavity of used or spent dialysate.

Figure 17:
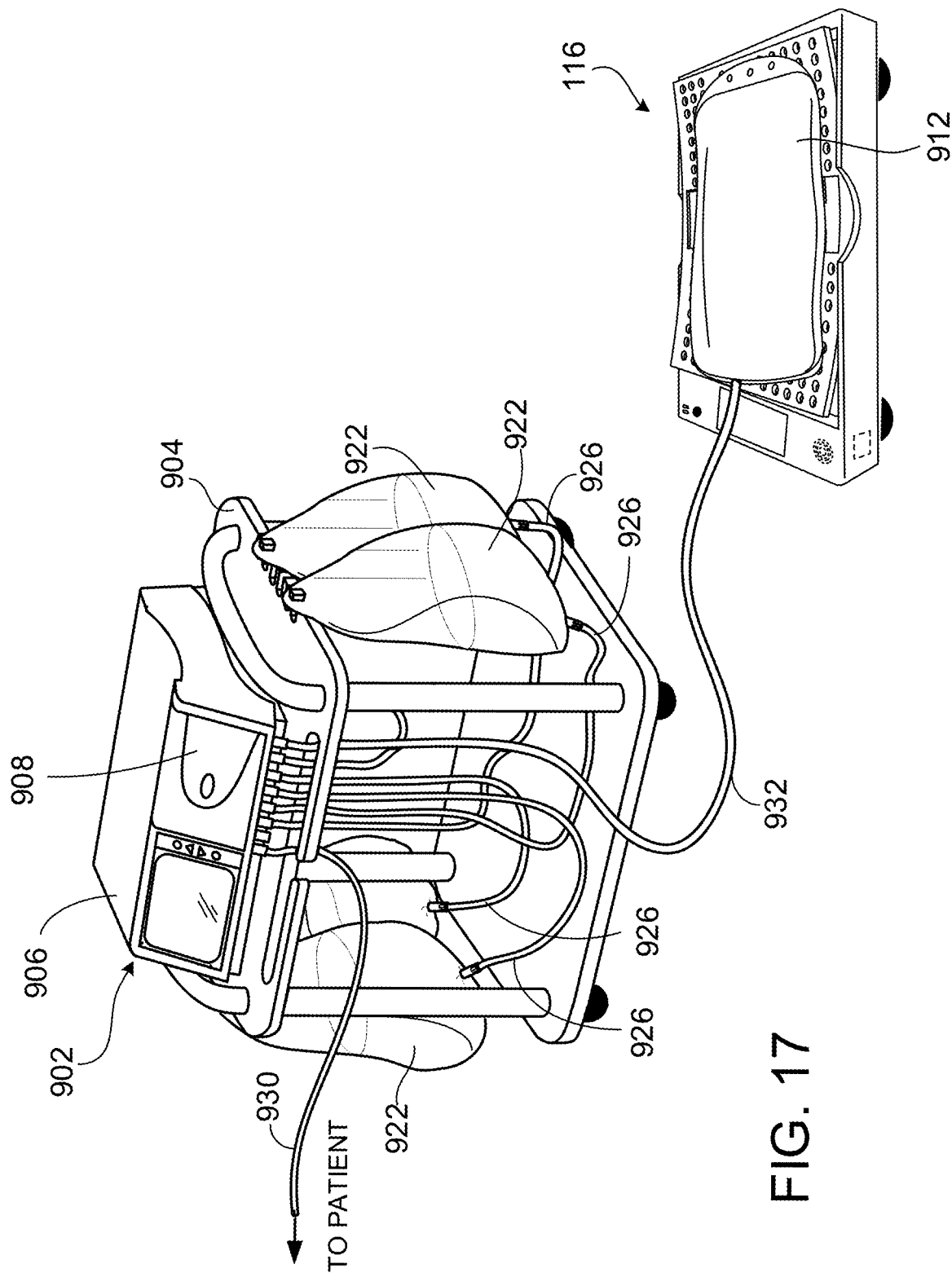
FIG. 17 is a perspective view of another example PD treatment system.

FIG. 17 depicts an example PD cycler 902 seated on a cart 904. The PD cycler 902 includes a housing 906, a door 908, and a cassette interface that contacts a disposable PD cassette when the cassette is disposed within a cassette compartment formed between the cassette interface and the closed door 908. Dialysate bags 922 are suspended from fingers on the sides of the cart 904. The dialysate bags 922 are connected to the cassette via dialysate bag lines 926. The dialysate bag lines 926 can be used to pass dialysate from dialysate bags 922 to the cassette during a fill phase of an APD treatment cycle. A patient line 930 and a drain line 932 are connected to the cassette. The patient line 930 can be connected to a patient's abdomen via a catheter and can be used to pass dialysate back and forth between the cassette and the patient's peritoneal cavity during use. The drain line 932 can be connected to drain bag 912 positioned on the basin system 116 and can be used to pass dialysate from the cassette to the drain bag 912 during use.

As described above, the basin system 116 can be used to measure and record one or more treatment data related the PD treatment, such as drain start time, drain end time, the amount of fluid drained during the treatment, the clarity of effluent drained during the treatment, dwell time, dialysate volume exchanged during treatment. In addition, as described herein, the basin system 116 can be used to detect and contain any leaks in the drain bag 912 that occur during the treatment. The treatment data collected by the basin system 116 can be used to confirm the accuracy of similar treatment data collected by the cycler 902 and can be used to calibrate the cycler 902. In some implementations, basin systems 116 used in conjunction with a cycler 902 during APD treatment have a larger tray 202 and basin 204 compared to systems 116 used during CAPD treatments in order to accommodate the larger and/or greater number of drain bags used during APD treatments.

In some implementations, drain bag(s) 912 used during APD are connected to hooks on cart 904 to support the drain bag(s) 912, and the basin system 116 is positioned underneath and in contact with the drain bag(s) 912. In some implementations, basin systems 116 used for APD treatments do not include a heating system (e.g., conductive core elements 218, 220 and heating elements 250, 252), as dialysate is automatically warmed by the cycler 902.

While the heating elements 250, 252 have been described as being automatically activated and deactivated based on signals received from the weight scale 206, other means of controlling the heating elements 250, 252 are possible. For example, in some implementations, the heating elements 250, 252 are controlled based on user input received by the control unit 242. For example, the user can use the graphical display 238 or the microphone 241 of the basin 204 to provide instructions to activate or deactivate the heating elements 250, 252. In some implementations, a user can set a temperature of the heating elements 250, 252 using the graphical display 238 or the microphone 241 of the basin 204. In some implementations, the system includes a mechanical switch that is activated when a predetermined amount of force is placed on the tray 202, such as when a dialysate bag 102 is placed on the tray 202, and the control unit 242 activates the heating elements 250, 252 in response to activation of the mechanical switch.

In some implementations, a magnet is positioned within the basin 204 and the system 116 includes a Hall effect sensor to control activation of the heating elements 250, 252. For example, when a threshold force is applied to the tray 202 (for example, by positioning a dialysate bag 102 on the tray 202), the conductive core elements 218, 220 are lowered into proximity of the magnet in the basin 204, which causes the Hall effect sensor to transmit a sensor to control unit 242. In response to receiving a signal from the Hall effect sensor indicating that a force has been applied to the tray 202, the control unit 242 activates the heating elements 250, 252 to heat the conductive core elements 218, 220.

In some implementations, the system 116 includes one or more ultrasonic range detectors and/or optical or laser detectors configured to measure the distance between the tray 202 and the bottom surface 246 of the basin 204 in order to control activation of the heating elements 250, 252. For example, when a threshold force is applied to the tray 202 that causes the tray 202 to be lowered within a threshold distance of the bottom surface 246 of the basin 204 (for example, by positioning a dialysate bag 102 on the tray 202), the ultrasonic, optical, or laser sensor(s) transmit a signal to control unit 242. In response to receiving a signal from the ultrasonic, optical, or laser sensor(s), the control unit 242 activates the heating elements 250, 252 to heat the conductive core elements 218, 220. Similarly, in some implementations, the system 116 includes one or more optical detectors configured to detect an air gap between the bottom of the tray 202 and the bottom surface 246 of the basin 204, and when a threshold force is applied to the tray 202 causing the tray 202 to be lowered into contact with the bottom surface 246 of the basin 204 (for example, by positioning a dialysate bag 102 on the tray 202), the optical detector(s) transmit a signal to control unit 242 indicating contact between the tray 202 and basin 204. In response to receiving a signal from the optical detector(s) indicating contact between the tray 202 and basin 204, the control unit 242 activates the heating elements 250, 252 to heat the conductive core elements 218, 220.

While the tray 202 has been depicted as including two conductive core elements 218, 220, other numbers of conductive core elements 218, 220 can be used. In addition, while basin 204 has been depicted as having two heating elements 250, 252, other numbers of heating elements can be used.

While the tray has been depicted as having two handles 214, 216, the tray can alternatively include a single handle or three or more handles. In addition, while the handles 214, 216 are depicted as being formed into the tray 202, one or more handles can be coupled to a surface of the tray.

While the basin system 116 has been depicted as including both contrast text 222 and an effluent sensor 248, in some implementations, the system 116 includes contrast text 222 and does not include an effluent sensor 248. In some implementations, includes an effluent sensor 248 and does not include contrast text 222.

In addition, while the effluent sensor has been described as being an optical sensor, in some implementations, the effluent sensor 248 is an ultrasonic sensor. An ultrasonic effluent sensor 248 can be used to detect the presence of one or more foreign substances in effluent, such fibrin or other particles in the effluent in the drain bag 112. In response to detecting foreign substances in the effluent using an ultrasonic effluent sensor 248, a signal indicating the presence of foreign substances in the effluent can be transmitted to the control unit 242, which, in response, can cause the graphical display 238 and/or the speaker 240 of the basin 204 to generate an alarm indicating foreign substances in the effluent.

While the effluent sensor 248 has been described as being activated in response to user input, in some implementations, the effluent sensor 248 is automatically operated by the control unit 242 without requiring user input. For example, in response to receiving a signal from the weight scale 206 indicating that a predetermined amount of time has elapsed since any weight increases were detected by the scale 206, indicating that the drain cycle is complete, the control unit 242 can activate the effluent sensor 248 to automatically scan the effluent contained in the drain bag 112 and transmit the results to the control unit 242. In some implementations, the effluent sensor 248 is configured to periodically scan the effluent at predetermined intervals throughout the draining process (e.g., every 10 to 15 minutes during the draining process).

While the leak detector 234 has been depicted as being formed of two metal rings 231, 233, other types of leak detectors can be used for detecting fluids leaked into the basin 204. For example, in some implementations, the leak detector includes two probes serving as positive and negative terminals. When electrically conductive fluid, such as dialysate or effluent, leaks into the chamber 236 and contacts the two probes of the leak detector 234, the leaked fluid bridges the gap between the probes and allows electrical current to flow from positive to negative terminals to complete a circuit. In response to completion of the circuit formed by the leak detector 234, the leak detector 234 transmits a signal to a computing device (e.g., control unit 242) indicating the presence of a leak.

In some implementations, the basin 204 includes a leak detector 234 having a pair of ultrasonic heads positioned opposite each other (e.g., in a formed between the scale 205 and the bottom surface 246 of the chamber 236), and when leaked fluid flows into the chamber and passes between the ultrasonic heads, the leak detector 234 transmits a signal to a computing device (e.g., control unit 242) indicating the presence of a leak.

In some implementations, the system 116 includes a leak detector 234 having a rotameter with an optical sensor that detects fluid as it moves a float in a chamber of the leak detector 234. In response to the optical sensor detecting that the float has moved within the chamber, the leak detector 234 transmits a signal to a computing device (e.g., control unit 242) indicating the presence of a leak.

In some implementations, the leak detector 234 includes a microphone, and a leak into the basin 204 is detected based on the control unit 242 receiving sound recordings from the leak detector and detecting that the recordings include a noise generated by fluid flowing past the leak detector 234 of the leak detector 234.

In some implementations, the leak detector 234 includes a turbine or wheel and when fluid leaked into the basin flows past the turbine or wheel of the leak detector 234, it causes the wheel or turbine to rotate. In response to rotation of the wheel or turbine, the leak detector 234 transmits a signal to a computing device (e.g., control unit 242) indicating the presence of a leak.

In some implementations, the leak detector 234 includes a piezoelectric sensor, and when fluid leaked into the basin 204 contacts the piezoelectric sensor of the leak detector 234 the leak detector 234 transmits a signal to a computing device (e.g., control unit 242) indicating the presence of a leak.

In some implementations, the leak detector 234 includes an optical flow sensor that generates a laser beam, and as fluid leaked into the basin 204 flows past the leak detector, the laser beam is interrupted, which is detected by the optical flow sensor. In response to the optical flow sensor detecting interruption of the laser beam, the leak detector 234 transmits a signal to a computing device (e.g., control unit 242) indicating the presence of a leak.

In some implementations, the leak detector 234 includes a thermal sensor that detects a change in temperature when fluid is leaked into basin 204. For example, the thermal sensor can detect when leaked fluid reduces the temperature of a hot spot in the basin. In response to the thermal sensor detecting a change in temperature caused by leaked fluid, the leak detector 234 transmits a signal to a computing device (e.g., control unit 242) indicating the presence of a leak.

While the stand 104 for hanging dialysate bags 102 during the fill phase of CAPD treatment has been depicted as being separate from the basin system 116, in some implementations a stand for hanging dialysate bags is integrated into the basin 204 of the basin system 116.

In addition, while the basin system 116 has been depicted as being placed on the floor next to the patient 110, the basin system 116 can be positioned on other surfaces during treatment. For example, the basin system 116 can be positioned on a chair or table near the patient 110 during treatment in order to position the basin system 116 within reach of the patient 110.

While the flow sensor 120 has been described as transmitting sensor data to the control unit 242 by interfacing with a port 274, 276 on the basin 204, in some implementations, the flow sensor 120 is wirelessly coupled to the control unit 242 of the basin 204 and transmits data to the control unit 242 wirelessly (e.g., using a Bluetooth or another near field communication connection). In some implementations, sensor data is transmitted from the flow sensor 120 to the control unit 242 in real time.

In addition, while the volume of fluid provided to the patient during a fill phase has been described as being measured using a flow sensor 120, in some implementations the amount of fluid provided to the patient 110 during the fill phase of treatment is measured using a load cell coupled to the stand 104. For example, at the beginning of the fill phase, the dialysate bag 102 can be hung from or otherwise attached to a load cell attached to stand 104. As fluid flows from the dialysate bag 102 to the patient 110 during the fill phase of treatment and, as a result, the weight of the dialysate bag 102 decreases, these changes in weight can be measured by the load cell on stand 104, and transmitted to the control unit 242. Based on this decrease in weight measured by the load cell on stand 104, the control unit 242 can determine a volume of dialysate provided to the patient during the fill phase of treatment.

Further, while the start time and end time of the fill phase have been described as being determined based on data received from the flow sensor 120, other methods of determining a fill start time and a fill end time can be used. For example, as previously discussed, a dialysate bag 102 containing fresh dialysate can be placed on tray 202 for heating by the basin system 116 prior to beginning the fill phase. Once the heating is complete, the dialysate bag 102 is removed from the tray 202 and is attached to stand 104 to begin the fill phase. The weight scale 206 can detect the decrease in force applied to the tray 202 resulting from removal of the dialysate bag 102 from the tray 202 after completion of heating the dialysate, and in response to detecting the reduction in force at the end of heating, can send a signal to the control unit 242 indicating a start time of the fill phase corresponding to the time the reduction in force was detected. Similarly, after the fill phase is complete, the emptied (or partially emptied) dialysate bag 102 can be returned to the tray 202 for measurement of the final weight of the dialysate bag 102. The weight scale 206 can detect an increase in force applied to the tray 202 resulting from the empty dialysate bag 102 being placed on the tray 202 at the end of the fill phase. In response to detecting the increase in force caused by placing the empty dialysate bag 102 on the tray 202 at the end of the fill phase, the weight scale 206 can send a signal to the control unit 242 indicating a end time of the fill phase corresponding to the time that the increase in force was detected due to placement of the empty dialysate bag 102 on the tray 202 at the end of the fill phase.

While user input has been described as being received by the control unit 242 through the graphical display 238 or microphone 241 of the basin 204, in some implementations, a user can transmit data to the control unit 242 using a remote computing device, such as a mobile device. For example, in some implementations, a user can interface with an application on a mobile device to provide treatment data to the control unit 242 of the basin 204 and provide commands for controlling one or more components of the basin 204 to the control unit 242. For example, the user can interface with an application on a computing device to provide data such as the dialysate concentration, the dialysate expiry date, dialysate volume exchanged during treatment, fill start time, fill end time, dwell time, drain start time, drain end time, the amount of fluid drained during the treatment, the clarity of effluent drained during the treatment In addition, while alarms, messages, and warning have been described as being provided to the user by the graphical display 238 and the speaker 240 of the basin 204, in some implementations, the control unit 242 can additionally or alternatively transmit alarms, messages, and warning to one or more remote computing devices. For example, the control unit 242 can transmit alarms, messages, and warnings as push notifications on a user's mobile device. In some implementations, the control unit 242 transmits alarms, messages, and warnings to a user's computing device for display in an application operating on the user's computing device.

While the components of the basin 204 have been described as being powered by a rechargeable battery, other power sources may be used to provide power to the basin 204. For example, the basin 204 may be powered by a power supply directly through connection of the power source to the power adapter 270 on the back of the basin 204 via a power cable.

While the control unit 242 has been described as transmitting treatment data to one or more remote computing devices for storage, in some implementations, the treatment data is additionally or alternatively stored on a local storage device of the basin system 116.

While the basin system 116 has been described as supporting both a dialysate bag 102 and a drain bag 112 during PD treatment, the basin system 116 can alternatively be used for supporting only the dialysate bag 102 during treatment or supporting only the drain bag 112 during treatment.

While the basin system 116 has been described as being used as part of a PD system 100 during PD treatment, the basin system 116 can also be used during other blood treatments including, but not limited, hemodialysis (HD) treatment, hemofiltration (HF) treatment, and hemodiafiltration (HDF).

FIG. 18 depicts an example blood treatment system 800 for performing one or more types of blood treatments, including HD, HF, and HDF treatments. As can be seen in FIG. 18, the blood treatment system 800 includes a blood treatment machine 802 to which a disposable blood component set 804 that forms a blood circuit is connected.

The blood treatment system 800 includes a fluid conditioning system 806 that is fluidly coupled to the blood treatment machine 802 and produces fluid to be used during the treatment, such as dialysate fluid, that can be provided to the blood treatment machine 802.

The blood treatment system 800 also includes a waste line 808 that is connected at a first end to the fluid circuit of the blood treatment machine 802 and is connected at a second end to a drain bag 812.

During treatment, arterial and venous patient lines of the disposable blood component set are connected to the patient and blood is circulated through various blood lines and components of the blood component set. At the same time, fresh dialysate is generated by the fluid conditioning system 806 and flows from the fluid conditioning system 806 to a dialyzer of the dialysis treatment machine via fluid lines. During treatment, toxins are removed from the patient's blood and collected in the dialysate flowed through the dialyzer. The filtered blood is then returned to the patient and the spent dialysate exiting the dialyzer is flowed back to the fluid conditioning system 806. A sorbent cartridge 814 of the fluid conditioning system 806, removes (e.g., filters out) toxic substances that have collected in the spent dialysate to produce "regenerated" dialysate (e.g., cleaned, unconditioned dialysate) that flows out of the sorbent cartridge 814. The regenerated dialysate exiting the sorbent cartridge 814 is further conditioned by the fluid conditioning system 806 to meet acceptable physiological properties and is then pumped back to the blood treatment machine 802 as "fresh" dialysate.

Once treatment is complete, the spent dialysate (and any additional fluid removed from the patient) is drained from the fluid circuits of the blood treatment machine 802 and the fluid conditioning system 806 through the waste line 808 and into drain bag 812. For example, one or more pumps of the blood treatment machine 802 and/or the fluid conditioning system 806 can be operated to draw fluid out of the fluid circuit(s) of the blood treatment machine 802 and/or the fluid conditioning system 806, through waste line 808, and into drain bag 812.

As can be seen in FIG. 18, the drain bag 812 of the blood treatment system 800 can be supported by a respective basin system 116 during the treatment. For example, the basin system 116 supporting the drain bag 812 can be used to measure a weight of fluid provided to the drain bag at the end of the treatment (e.g., by using weight scale 206 of basin system 116). The basin system 116 can also be used to detect a clarity of the spent dialysate contained in the drain bag 812 (e.g., using contrast text 222 and/or effluent sensor 248, as described above). The basin system 116 can also be used to detect if leakage from the drain bag 812 has occurred during treatment using a leak detector positioned in the basin 204 of the basin system 116 (e.g., leak detector 234).

In addition, the basin system 116 can be used to record and automatically transmit data related to the blood treatment to a remote computing device. For example, the basin system supporting the drain bag 812 can record and transmit an amount of spent dialysate drained during treatment, any leakages from the drain bag 812 detected during treatment, a clarity of the spent dialysate in the drain bag 812, and an end time for the treatment (e.g., the time corresponding to the last increase in weight of the drain bag 812 as detected by a weight scale of the basin system 116, such as weight scale 206). In some implementations, the treatment data is transmitted from the basin system 116 to one or more remote computing devices in real time. Recording and transmitting treatment data using the basin system 116 is described in detail above with reference to FIGS. 2-14.

While FIG. 18 depicts using a single basin system 116 to support a drain bag 812 during an HD, HF, or HDF treatment, in some implementations, a basin system can be used to support a container of dialysate fluid (or other fluid used by the fluid conditioning system 806 to generate dialysate) during treatment using the blood treatment machine 802. In addition, basin systems 116 used to support dialysate bags can include a heating system (e.g., conductive core elements 218, 220 and heating elements 250, 252) while the basin system used to support the drain bag 812 does not include a heating system.

Further, while the basin system 116 has been illustrated as being separate from the blood treatment machine 802 and fluid conditioning system 806, basin systems could alternatively be included as sub-systems of the blood treatment machine 802 and/or the fluid conditioning system 806. For example, one or more basin systems could be attached to a bottom portion of the blood treatment machine 802 for holding one or more drain bags 812.

What is claimed is:

1. A system comprising:
a curved tray configured to support a medical fluid bag during a medical treatment, the curved tray comprising a plurality of openings therethrough;
a medical fluid collection basin removably coupled to the curved tray and configured to collect medical fluid leaked from the medical fluid bag during the medical treatment;
a leak detector coupled to a surface of the medical fluid collection basin and configured to detect that fluid has leaked from the medical fluid bag into the medical fluid collection basin; and
a control unit configured to receive treatment data related to the medical treatment.

2. The system of claim 1, wherein the control unit is configured to receive a signal from the leak detector indicating that a medical fluid leak occurred during the medical treatment.

3. The system of claim 1, wherein the control unit is configured to automatically transmit the treatment data to a remote computing device, wherein the treatment data comprises at least one of a drain start time, a drain end time, a drain duration, a volume drained, and leakages detected.

4. The system of claim 1, wherein:
the medical fluid collection basin comprises a port; and
the control unit is configured to transmit the treatment data to a portable memory device interfacing with the port of the medical fluid collection basin.

5. The system of claim 4, wherein:
the port is configured to connect to a flow sensor that is configured to measure fluid flow along a fluid line fluidly coupled to a dialysate bag and a peritoneal cavity of a patient; and
the control unit is configured to determine a fill volume based on the fluid flow measured by the flow sensor.

6. The system of claim 1, wherein the medical fluid collection basin comprises:
a drain opening therethrough;
a drain plug configured to be inserted into and seal the drain opening during the medical treatment; and
a curved inner surface that slopes towards the drain opening.

7. The system of claim 6, wherein the curved inner surface of the medical fluid collection basin comprises a clear material.

8. The system of claim 1, wherein:
the leak detector is positioned proximate a center of the medical fluid collection basin; and
a curved inner surface that slopes towards the center of the medical fluid collection basin.

9. The system of claim 8, wherein the leak detector comprises a pair of metal rings surrounding a weight scale coupled to the medical fluid collection basin.

10. The system of claim 1, wherein the curved tray comprises a central channel configured to direct liquid leaked from the medical fluid bag into the medical fluid collection basin.

11. The system of claim 1, wherein the curved tray comprises handles.

12. The system of claim 1, wherein the curved tray comprises text on a surface of the curved tray configured to be in contact with the medical fluid bag.

13. The system of claim 1, further comprising a weight scale coupled to the medical fluid collection basin and configured to contact the curved tray, wherein the weight scale is configured to detect a weight of fluid contained within a medical fluid bag positioned on the curved tray.

14. The system of claim 13, wherein the control unit is configured to:
receive data from the weight scale and to determine, based on the data, an amount of fluid contained within the medical fluid bag positioned on the curved tray; and
determine, based on data received from the weight scale, treatment data comprising at least one of a drain start time, a drain end time, or a drain duration.

15. The system of claim 1, wherein the medical fluid collection basin comprises:
a speaker;
a microphone communicably coupled to the control unit and configured to receive user input regarding one or more treatment parameters; and
a graphical display configured to display a graphical user interface.

16. The system of claim 1, wherein:
the medical fluid bag is a drain bag configured to receive effluent draining out of a patient during the medical treatment; and
the system further comprises an effluent sensor coupled to the medical fluid collection basin and configured to detect one or more characteristics of effluent draining out of the patient into the medical fluid bag during the medical treatment, wherein the effluent sensor is an optical sensor or an ultrasonic sensor.

17. The system of claim 1, further comprising a heater configured to heat a medical fluid contained in the medical fluid bag positioned on the curved tray.

18. The system of claim 17, wherein:
the medical fluid bag comprises a dialysate bag containing dialysate to be provided to a patient during the medical treatment; and
the heater is configured to heat the dialysate to a predetermined temperature.

19. The system of claim 17, wherein the heater comprises:
a conducting core element extending through the curved tray; and
a heating element coupled to a surface of the medical fluid collection basin, wherein contact between the conducting core element and the heating element heats the conducting core element.

20. The system of claim 19, further comprising one or more depressible members coupled to the medical fluid collection basin and configured to contact the curved tray, wherein placing a filled fluid bag on the curved tray compresses the one or more depressible members and causes the conducting core element to contact the heating element.

21. The system of claim 1, wherein the medical treatment is a peritoneal dialysis treatment, a hemodialysis treatment, a hemofiltration treatment, or a hemodiafiltration treatment.

22. The system of claim 1, wherein the medical fluid bag contains dialysate or effluent drained from a patient during the medical treatment.

23. A method of recording treatment data related to a medical treatment, the method comprising:
positioning a medical fluid bag on a tray removably coupled to a basin device;
flowing fluid into the medical fluid bag during the medical treatment;
detecting leakage of fluid from the medical fluid bag using a leak detection sensor positioned on a surface of the basin device; and
automatically transmitting treatment data from a control unit of the basin device to a remote computing device, the treatment data indicating that a medical fluid bag leak has occurred during the medical treatment.

* * * * *